US012232540B2

(12) United States Patent
Cohen

(10) Patent No.: US 12,232,540 B2
(45) Date of Patent: Feb. 25, 2025

(54) METHODS AND DEVICES FOR DELIVERING AND MONITORING OF TOBACCO, NICOTINE, OR OTHER SUBSTANCES

(71) Applicant: JUUL Labs, Inc., San Francisco, CA (US)

(72) Inventor: Gal A. Cohen, Mill Valley, CA (US)

(73) Assignee: JUUL Labs, Inc., Washington, DC (US)

( * ) Notice: Subject to any disclaimer, the term of this patent is extended or adjusted under 35 U.S.C. 154(b) by 554 days.

(21) Appl. No.: 17/520,032

(22) Filed: Nov. 5, 2021

(65) Prior Publication Data

US 2022/0053837 A1 Feb. 24, 2022

Related U.S. Application Data

(63) Continuation of application No. 16/725,981, filed on Dec. 23, 2019, now Pat. No. 11,166,495, which is a continuation of application No. 14/461,284, filed on Aug. 15, 2014, now Pat. No. 10,517,530, which is a continuation-in-part of application No. 14/012,952, filed on Aug. 28, 2013, now abandoned.

(60) Provisional application No. 61/694,046, filed on Aug. 28, 2012.

(51) Int. Cl.
*A24F 40/65* (2020.01)
*A24F 40/51* (2020.01)
*A61B 5/00* (2006.01)
*A61B 5/08* (2006.01)
*A61B 5/145* (2006.01)
*G01N 33/497* (2006.01)

(52) U.S. Cl.
CPC ............. *A24F 40/65* (2020.01); *A24F 40/51* (2020.01); *A61B 5/082* (2013.01); *A61B 5/14507* (2013.01); *A61B 5/14546* (2013.01); *A61B 5/486* (2013.01); *G01N 33/497* (2013.01); *G01N 2033/4975* (2013.01)

(58) Field of Classification Search
CPC .......... A24F 40/51; A24F 40/65; A61B 5/082; A61B 5/14507; A61B 5/14546; A61B 5/486; G01N 2033/4975; G01N 33/497
See application file for complete search history.

(56) References Cited

U.S. PATENT DOCUMENTS

| 10,111,467 B1 | 10/2018 | Arnel et al. |
| 2002/0142291 A1 | 10/2002 | Bauer et al. |
| 2003/0004426 A1 | 1/2003 | Melker et al. |
| 2003/0149372 A1 | 8/2003 | Smith et al. |
| 2005/0081601 A1* | 4/2005 | Lawson ............... G01N 33/497 73/23.3 |
| 2008/0138423 A1 | 6/2008 | Gonda |

(Continued)

OTHER PUBLICATIONS

U.S. Appl. No. 14/461,284, filed Aug. 15, 2014, now U.S. Pat. No. 10,517,530.
U.S. Appl. No. 14/012,952, filed Aug. 28, 2013, now U.S. Pat. No. 2014-0060552.
U.S. Appl. No. 16/725,981, filed Dec. 23, 2019, now U.S. Pat. No. 11,166,495.

(Continued)

*Primary Examiner* — Jennifer Wecker

(57) ABSTRACT

Methods, systems, and devices are described for providing risk evaluation and mitigation strategies for use with modified risk products or other tobacco products, and in particular, associated with nicotine and tobacco products.

14 Claims, 13 Drawing Sheets

(56) References Cited

U.S. PATENT DOCUMENTS

| | | | |
|---|---|---|---|
| 2008/0319025 A1* | 12/2008 | Sellers | A61K 31/465 514/343 |
| 2010/0209897 A1* | 8/2010 | Utley | A24F 47/00 434/238 |
| 2011/0036346 A1 | 2/2011 | Cohen et al. | |
| 2011/0226236 A1 | 9/2011 | Buchberger | |
| 2011/0263947 A1 | 10/2011 | Utley et al. | |
| 2012/0291791 A1 | 11/2012 | Pradeep | |
| 2012/0318882 A1 | 12/2012 | Abehasera | |
| 2013/0174842 A1 | 7/2013 | Young et al. | |
| 2013/0220315 A1* | 8/2013 | Conley | A24F 40/44 128/202.21 |
| 2014/0060552 A1* | 3/2014 | Cohen | A61M 15/06 131/273 |
| 2014/0378790 A1* | 12/2014 | Cohen | A61B 5/082 600/300 |
| 2015/0173419 A1* | 6/2015 | Tu | A24F 40/51 131/329 |

OTHER PUBLICATIONS

Andrew Gregory (Jun. 12, 2013) "E-Cigarettes to go on Prescription Under Move to Class them as Medicines", Mirror, Available at: <http://www.mirror.co.uk/news/uk-news/e-cigarettes-go-prescription-under-move-1949018>, 8 pages.

SRNT Subcommittee on Biochemical Verification, (May 2002) "Biochemical Verification of Tobacco Use and Cessation", Nicotine and Tobacco Research, 4(2):149-159.

Hurt et al. (2009) Treating Tobacco Dependence in a Medical Setting, CA: A Cancer Journal for Clinicians, 59(5):314-326.

Caponnetto et al. (Dec. 20, 2011) "Successful smoking cessation with electronic cigarettes in smokers with a documented history of recurring relapses: a case series" Journal of Medical Case Reports, 5:585 (6 pages).

Ghenadii, Korotcenkov, (2010), Chemical Sensors: Fundamentals of Sensing Materials vol. 3, pp. 351-375.

* cited by examiner

Prescriber / Dispenser Authorization and Verification

Prescription Process and Verification

Prescription Process and Verification

| Biochemical Markers | Cut-off Value |
|---|---|
| Carbon Monoxide | |
| ECO (ppm) | 8 |
| COHb (%) | 1.6 |
| Nicotine (ng/ml) | |
| Plasma | 2.3 |
| Saliva | 21.8 |
| Urine | 58.6 |
| Cotinine (ng/ml) | |
| Plasma | 13.7 |
| Saliva | 14.2 |
| Urine | 49.7 |
| Thiocyanate | |
| Plasma (µmol/l) | 78.0 |
| Saliva (mmol/l) | 1.64 |
| Urine (µmol/l) | 118.0 |

Fig. 3E

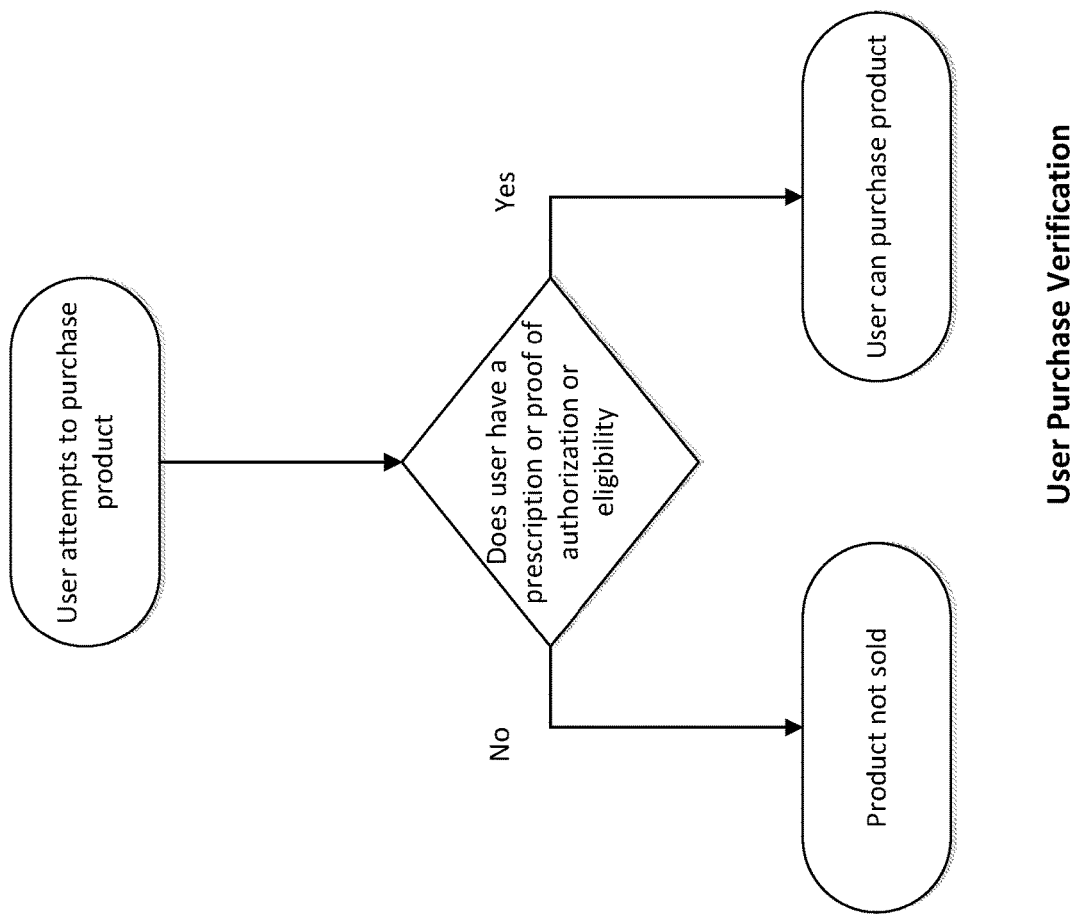

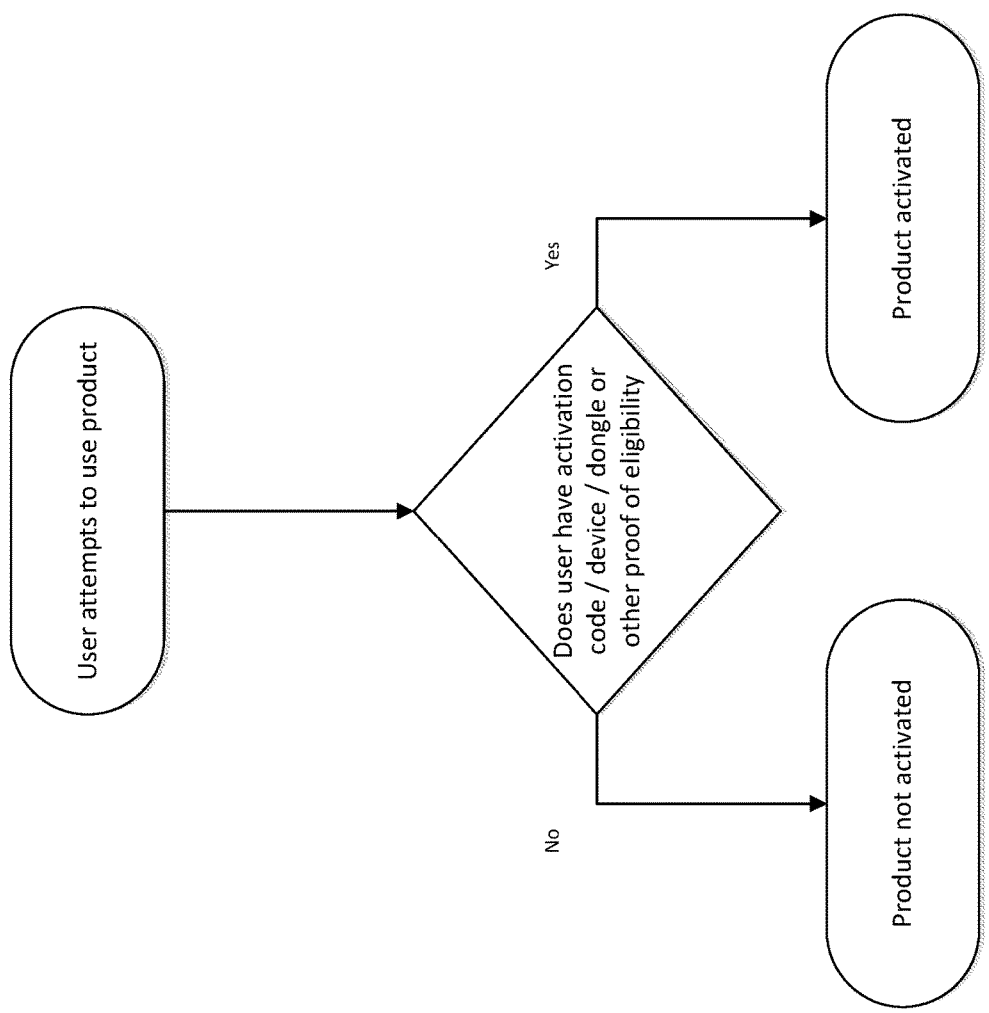

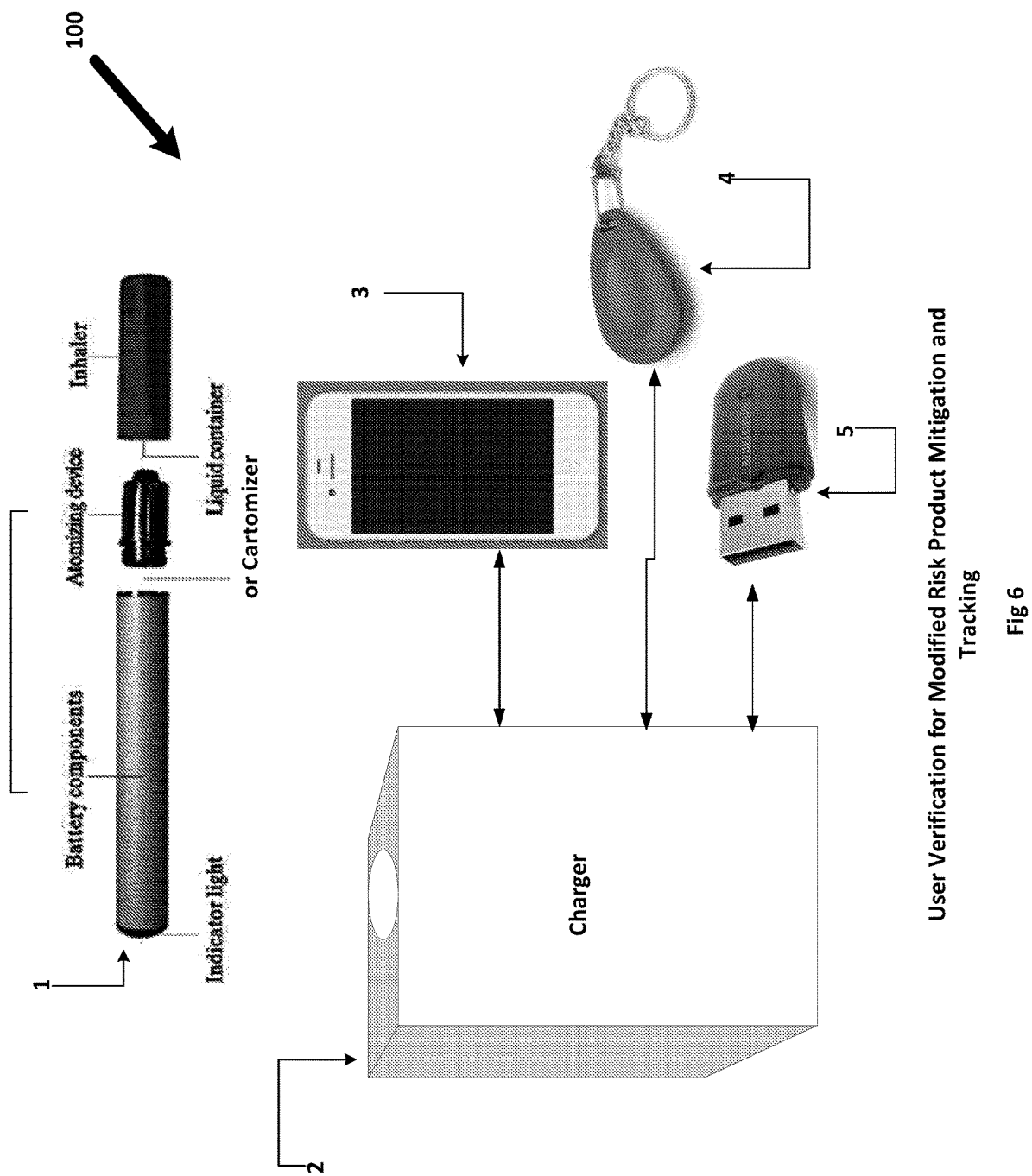

Program compliance verification

METHODS AND DEVICES FOR DELIVERING AND MONITORING OF TOBACCO, NICOTINE, OR OTHER SUBSTANCES

CROSS-REFERENCE TO RELATED APPLICATIONS

This application is a continuation of U.S. patent application Ser. No. 16/725,981 filed Dec. 23, 2019, and entitled "METHODS AND DEVICES FOR DELIVERY AND MONITORING OF TOBACCO, NICOTINE, OR OTHER SUBSTANCES," which is a continuation of U.S. patent application Ser. No. 14/461,284 filed Aug. 15, 2014, now U.S. Pat. No. 10,517,530, and entitled "METHODS AND DEVICES FOR DELIVERY AND MONITORING OF TOBACCO, NICOTINE, OR OTHER SUBSTANCES," which is a continuation-in-part of U.S. patent Application Ser. No. 14/012,952 filed Aug. 28, 2013, and entitled "METHODS AND DEVICES FOR DELIVERY AND MONITORING OF TOBACCO, NICOTINE, OR OTHER SUBSTANCES," which claims the benefit of U.S. Provisional Patent Application No. 61/694,046 filed Aug. 28, 2012, and entitled "METHODS AND DEVICES FOR DELIVERY AND MONITORING OF TOBACCO, NICOTINE, OR OTHER SUBSTANCES," each of which is herein incorporated by reference in its entirety.

BACKGROUND OF THE INVENTION

The use of tobacco products and the harmful side effects of smoking tobacco and nicotine consumption continue to gain increasing attention worldwide. As more regulations come into effect regarding smoking in the work place or in public, interest in developing alternative methods of protecting public health and providing cessation products and methods is growing significantly. As with most new therapies or drugs, the federal government has issued regulations intended to protect the public, with enforcement authority granted to the U.S. Food and Drug Administration (FDA).

SUMMARY OF THE INVENTION

It is generally understood that the mission of the US Food and Drug Administration (FDA) is to advance the public health by helping to speed the innovations that make medicines and most foods more effective, safer, and more affordable; and help the public get accurate, science-based information they need to use those medicines and foods to improve their health.

In June, 2009, The Family Smoking Prevention and Tobacco Control Act was signed into law, creating "The Center for Tobacco Products", a tobacco control center within the FDA, having the authority to regulate tobacco industry in the U.S., by regulating the content, commercial marketing, sale and distribution of tobacco products within the United States. The law also requires tobacco companies and importers to reveal all product ingredients and seek FDA approval for any new tobacco products.

Under its new-found, expanded authority, the FDA now has the ability to control the commercial sale and distribution of traditional tobacco products, including cigarettes, pipe tobacco, and cigars, as well as new tobacco and nicotine related products, including; electronic nicotine vaporizers, (e.g. the electronic cigarette); and products with potentially modified safety risk relative to cigarettes. These products have new regulatory pathways associated with them, including those proscribed under Section 911 (modified risk tobacco products.)

When considering whether to allow the marketing of modified risk products or other novel or new but substantially equivalent tobacco products, FDA must consider the benefit to health of individuals and the population as a whole, including: "the increased or decreased likelihood that existing users of tobacco products who would otherwise stop using such products will switch to the tobacco product that is the subject of the application; the increased or decreased likelihood that persons who do not use tobacco products will start using the tobacco product that is the subject of the application; and the risks and benefits to persons from the use of the tobacco product that is the subject of the application as compared to the use of products for smoking cessation approved under chapter V to treat nicotine dependence."

One potential approach for FDA to address the benefits to health of individuals and the population could be to require Risk Evaluation and Mitigation Strategies (REMS) be put in place for modified risk products or other tobacco products as a prerequisite for marketing approval.

There are essentially three components to a REMS program: 1. A medication guide or patient insert; 2. A communication plan for healthcare providers; and 3. Elements to assure safe use, (ELASU). A drug's REMS program may not require the provision of all three components, as the specific components a REMS program employs will vary based on the severity of the risks, the population likely to be exposed, and other factors. In fact, the most common REMS only require the provision of a medication guide.

While REMS components are not uniform, some currently do, or in the future, may contain new provisions and requirements for physicians and other certified health care providers. For REMS requiring ETASU, clinicians may be required to: Obtain and dispense drugs through specific distribution channels; Possess specific training, education, experience, or certification(s) in order to prescribe these drugs; Enroll patients in registry programs; and, Issue mandatory, time-sensitive reports of patient responses to treatment.

It is possible that one's ability to prescribe and dispense certain medications, even some that have been on the market for years, could be contingent upon compliance with these REMS provisions.

Applicant has developed novel methods and devices for the delivery and monitoring of tobacco, nicotine and other substances that will meet or exceed any potential federal regulation in this field.

Provided herein is a method of protecting public health comprising: increasing the likelihood that a first subject or a second subject will stop using a tobacco product by providing a modified risk product or other tobacco product for administration to the first subject addicted to the tobacco product wherein the first subject has previously failed nicotine replacement therapy.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided, or a subject's eligibility is verified by a physician, a nurse, a pharmacist, an accredited healthcare provider, or an employee of a convenience or retail store.

In some embodiments, the product is prescribed, provided, or a subject's eligibility is verified by an internet or wireless based application, service or business, or by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine, nicotine by-product levels, CO levels, or other biomarker levels are above or consistent with levels expected for a tobacco or nicotine user.

In some embodiments, the subject compliance verification comprises collecting and sending samples, taken before (and/or in some variations, after) being provided a modified risk product, for analysis to an accredited testing facility, and measuring the difference between said samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising: increasing the likelihood that a first subject or a second subject will stop using a tobacco product by providing a modified risk product or other tobacco product for administration to the first subject addicted to the tobacco product only after at least one failed attempt by the first subject to quit using such tobacco product. In general, modified risk products or other tobacco products may include tobacco and/or nicotine delivery devices including, for example: an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the previously failed at least one attempt to quit using said tobacco product comprises, abstinence, nicotine gum, nicotine oral spray, nicotine inhaler, nicotine nasal spray, nicotine lozenge, nicotine dermal patch, Bupropion™, Chantix™, or comparable oral nicotine replacement product.

In some embodiments, the product is prescribed, provided, administered, or subject eligibility verified by a physician, a nurse, a pharmacist, or an accredited healthcare provider, or an employee of a convenience or retail store.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising increasing the likelihood that a first subject or a second subject will stop using a tobacco product by providing a modified risk product or other tobacco product for administration to the first subject addicted to the tobacco product only after the modified risk product or other tobacco product is prescribed to the first subject.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the product is prescribed by a physician, a nurse, a pharmacist, or an accredited healthcare provider.

In some embodiments, the risk evaluation and mitigation strategy incorporates a means of subject compliance verification.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising decreasing the likelihood that a second subject not using a tobacco product will start using the tobacco product by providing a modified risk product or other tobacco product for administration to the first subject addicted to the tobacco product wherein the first subject has previously failed nicotine replacement therapy.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the previously failed attempt to quit using said tobacco product comprises, abstinence, nicotine gum, nicotine oral spray, nicotine inhaler, nicotine nasal spray, nicotine lozenge, nicotine dermal patch, Bupropion, Chantix, or comparable oral nicotine replacement product.

In some embodiments, the product is prescribed, provided or subject eligibility verified by a physician, a nurse, a pharmacist, or an accredited healthcare provider.

In some embodiments, the product is provided or subject eligibility verified by an employee of a convenience or retail store.

In some embodiments, the product is provided, or subject eligibility verified by an internet based application, service or business.

In some embodiments, the product is provided or subject eligibility verified by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine, nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising decreasing the likelihood that a second subject not using a tobacco product will start using the tobacco product by providing a modified risk product or other tobacco product for administration to the first subject addicted to the tobacco product only after at least one failed attempt by the first subject to quit using such tobacco product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the previously failed attempt to quit using said tobacco product comprises, abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided or subject eligibility verified by a physician, a nurse, a pharmacist, or an accredited healthcare provider.

In some embodiments, the product is provided or subject eligibility verified by or an employee of a convenience or retail store.

In some embodiments, the product is provided, or subject eligibility verified by an internet based application, service or business.

In some embodiments, the product is provided or subject eligibility verified by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising decreasing the likelihood that a second subject not using a tobacco product will start using the tobacco product or an alternative tobacco product, by providing a modified risk product or other tobacco product for administration to the first subject addicted to the tobacco product, only after the modified risk product or other tobacco product is prescribed to the first subject.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the product is prescribed by and subject eligibility verified by a physician, a nurse, a pharmacist, or an accredited healthcare provider.

In some embodiments, the product is provided or subject eligibility verified by or an employee of a convenience or retail store.

In some embodiments, the product is provided, or subject eligibility verified by an internet based application, service or business.

In some embodiments, the product is provided or subject eligibility verified by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of treating a first subject addicted to a tobacco product, the method comprising administering to the first subject who has previously failed nicotine replacement therapy, a modified risk product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by an employee of a convenience or retail store.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by or an employee of a convenience or retail store.

Provided herein is a method of treating a first subject addicted to a tobacco product, the method comprising administering to the first subject a modified risk product or other tobacco product only after at least one failed attempt by the first subject to quit using such tobacco product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by an employee of a convenience or retail store.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method of treating a first subject addicted to a tobacco product, the method comprising administering a modified risk product or other tobacco product to the first subject only after the modified risk product or other tobacco product is prescribed to the first subject.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the modified risk product or other tobacco product is prescribed and administered by a physician, a nurse, a pharmacist, or an accredited healthcare provider.

In some embodiments, the product is administered by an accredited employee of a convenience or retail store, or an employee of an accredited convenience or retail store.

In some embodiments, the product is administered by an internet or wireless based application, service or business.

In some embodiments, the product is administered by a call center or phone based application service or business.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood, expelled breath, saliva, hair, and/or urine.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method for increasing the likelihood that the first subject or a second subject will stop using the tobacco product.

Provided herein is a method for decreasing the likelihood that a second subject not using the tobacco product will start using the tobacco product.

Provided herein is a method for verifying the at least one prior failed attempt to stop using tobacco products prior to the modified risk product or other tobacco product being provided to a first subject.

In some embodiments, the verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user after verification that the subject had previously attempted to stop using tobacco products.

In some embodiments, the previously failed attempt may have comprised using abstinence, nicotine gum, nicotine oral spray, nicotine inhaler, nicotine nasal spray, nicotine lozenge, nicotine dermal patch, Bupropion®, Chantix®, or comparable oral nicotine replacement product.

Provided herein is a method for verifying that a first subject meets at least one eligibility requirement for use of a modified tobacco risk product.

Provided herein is a method for verifying a subject's eligibility requirement comprising: possession of an eligibility card, meeting qualifications for the eligibility card, possessing a valid verification code, possessing a physician-provided eligibility record, possessing a pharmacist-provided eligibility record, and passing a pharmacist-provided eligibility evaluation.

In some embodiments of a method having an eligibility requirement, the identity verification step comprises at least one of:
evidence of meeting a minimum age requirement,
evidence of a previously failed nicotine replacement therapy, and
evidence of a at least one failed attempt by the patient to quit using such tobacco product,
electronic or telephonic verification of a unique subject eligibility card or code identifier,
software verification of a unique subject eligibility card or code identifier,
electronic fingerprint verification of an eligible subject,
an activation code, or
an electronic dongle, electronic security key fob, or equivalent.

Provided herein is a method for verifying a subject's eligibility requirement wherein the verifying step is performed by a physician, a nurse, a pharmacist, an accredited healthcare provider an accredited employee of a convenience or retail store, or an employee of an accredited convenience or retail store.

Provided herein is a method for providing a prescription for a modified risk product, wherein said prescription is provided by a qualified healthcare provider.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

Provided herein is a method of verifying eligibility of a first subject addicted to a tobacco product, to be provided with a modified risk product, the method comprising, measuring nicotine levels, nicotine levels, CO levels, or other biomarker levels present in the system of a first subject prior to administration of said modified risk product or other tobacco product and confirming that said nicotine levels, nicotine levels, CO levels, or other biomarker levels are above or consistent with those of a tobacco or nicotine product user.

In some embodiments the method of verifying eligibility comprises; measuring nicotine levels, nicotine levels, CO levels, or other biomarker levels in blood samples, expelled breath samples, saliva samples, hair samples, and urine samples.

Provided herein is a method of monitoring compliance of a first subject addicted to a tobacco product and participating in a REMS program comprising a modified risk product, the method comprising, measuring nicotine levels, nicotine levels, CO levels, or other biomarker levels of a first subject prior to administration of said modified risk product or other tobacco product and measurement of nicotine levels, nicotine levels, CO levels, or other biomarker levels after administration of said modified risk product, and comparing said prior nicotine prior levels, nicotine levels, CO levels, or other biomarker levels to anticipated nicotine levels, nicotine levels, CO levels, or other biomarker levels after administration of said modified risk product.

In some embodiments, a method of monitoring comprises; using an electronic signature to track the pattern of use of a vaporizer, electronic cigarette, or other modified risk product or other tobacco product wherein said product transmits a record of use over a given period of time.

In some embodiments, a record of use comprises levels of nicotine consumed, times, and dates it was consumed.

In some embodiments, the record of use is stored to a data storage device and later downloaded for use by a qualified healthcare provider or REMS monitor or administrator.

In some embodiments, the record of use is transmitted wirelessly to a data storage device and later downloaded for use by a qualified healthcare provider or REMS monitor or administrator.

In some embodiments, the record of use is stored within the device, and later downloaded for use by a qualified healthcare provider or REMS monitor.

In some embodiments, the record of use may be wirelessly transmitted from a data storage device or a component of the modified risk product or other tobacco product to a remote location for use by a qualified healthcare provider or REMS monitor or administrator.

Provided herein is a method of monitoring the use of a modified risk product or other tobacco product by a first subject addicted to a tobacco product, the method comprising, requiring an identification recognition system be activated before use of a modified risk product or other tobacco product can occur.

In some embodiments, the identification recognition system comprises a fingerprint scanner, a lip print scanner, face recognition, a retinal scan, a combination code, an activation code, security key fob, or dongle.

In some embodiments, the identification recognition system comprises an electronic application for a smartphone, laptop, desktop, or tablet computing device, capable of communicating with the modified risk product or other tobacco product by a wireless communication system.

In some embodiments, the identification recognition system must be within a fixed distance of the modified risk product or other tobacco product for product to continue to work.

In some embodiments, the identification recognition system must be within about 5 to 20 feet of the modified risk product.

In some embodiments, the identification recognition system must be within 10 feet of the modified risk product.

In some embodiments, the identification recognition system must be within 5 feet of the modified risk product.

Provided herein is a method of protecting the public health comprising increasing the likelihood that a first subject will stop using a tobacco product by providing a modified risk product or other tobacco product for administration to the first subject addicted to the tobacco product wherein the modified risk product or other tobacco product provides a faster onset of nicotine delivery, or a higher peak level of nicotine delivery.

Provided herein is a method of risk mitigation wherein the potential risk of misuse or abuse of a modified risk product or other tobacco product is ranked or stratified in comparison to other tobacco products.

In some embodiments, the relative potential risk of the modified risk product or other tobacco product is determined by comparing the pharmacokinetic profile of the modified risk product or other tobacco product to nicotine.

In some embodiments the pharmacokinetic profile of the modified risk product or other tobacco product is determined by the maximum plasma concentration (Cmax) of nicotine, compared to a cigarette.

In some embodiments the pharmacokinetic profile of the modified risk product or other tobacco product is determined by the time after administration of the product for nicotine to reach maximum plasma concentration (Tmax), compared to a cigarette.

In some embodiments the pharmacokinetic profile of the modified risk product or other tobacco product is determined by the rate-of-increase of nicotine delivery or concentration in the plasma of a subject compared to a cigarette.

In some embodiments, the relative potential risk of the modified risk product or other tobacco product is determined by comparing the nicotine concentration of the modified risk product or other tobacco product other nicotine products in the market.

In some embodiments, the relative potential risk of the modified risk product or other tobacco product is ranked by ease of access associated with the prescriber/administrator.

In some embodiments, the relative potential risk of the modified risk product or other tobacco product is ranked by ease of access through various distribution channels.

In some embodiments the modified risk product or other tobacco product comprises vaporizing tobacco leaves above their pyrolytic temperature.

In some embodiments the modified risk product or other tobacco product comprises heating tobacco leaves below their pyrolytic temperature.

In some embodiments the modified risk product or other tobacco product comprises vaporization of a nicotine salt.

In some embodiments the modified risk product or other tobacco product comprises heating of a nicotine salt below its pyrolytic temperature.

Provided herein is a method of protecting the public health wherein the provider of a modified risk product or other tobacco product is subject to a compliance verification system.

In some embodiments, the provider verification is performed by an independent auditor.

Provided herein is a system for verification of subject eligibility, tracking, and reporting use of a modified risk product or other tobacco product comprising: an electronic cigarette, an electronic pipe, an electronic cigar, an electronic water pipe, or an electronic vaporizer, comprising a battery, an atomizer, electronic circuitry, a memory storage device for tracking components of usage activity, a means of memory transfer, and a charging circuit, a charger base station comprising a memory storage device, a means for receiving data from said modified risk product or other tobacco product memory storage device and transmitting said data to a third party, activation software for recognition of a specific device, keyed to said charger base, capable of interfacing with an external device, wherein said external device comprises; a smart phone, computer, electronic fob, electronic dongle, and a wireless communication device, e.g.: Bluetooth device.

In some embodiments, the system is used in combination with a risk evaluation and mitigation strategy.

In some embodiments, the system comprises activation means, for recognition and verification of a subject to establish user eligibility prior to use.

In some embodiments, the system is used to verify subject compliance for use of a modified risk product.

In some embodiments the system comprises a means for validating overall success of the risk mitigation product when used with the risk evaluation and mitigation strategies.

In general, in one embodiment, a method of providing a verification of eligibility for use or purchase of a tobacco product includes: (1) administering a diagnostic test to a subject; (2) determining whether the subject has previously used a tobacco product based upon results of the diagnostic test; and (3) providing a verification of eligibility for use or purchase of a tobacco product if results for the diagnostic test indicate that the subject has previously used a tobacco product.

This and other embodiments can include one or more of the following features. The step of determining can include determining from a saliva, blood, or urine test for nicotine, cotinine, or nicotine by-products. The step of determining can include determining from a carbon monoxide breath analysis. The step of determining can include determining if the subject's breath has a reading of greater than 5 ppm CO which can indicate that the subject previously used a tobacco product. The step of determining can include determining if the subject's breath has a reading of greater than 10 ppm which can indicate that the subject previously used a tobacco product. The step of determining can include determining whether the subject has consumed a tobacco product within the last 24 hours. The step of determining can include determining whether the subject has consumed a tobacco product on a regular basis, and the step of providing a verification of eligibility can include providing the verification for eligibility only if the subjected has consumed the tobacco product on a regular basis. The step of determining can include determining whether the subject has previously consumed combustible tobacco. The step of determining can include determining whether the subject has previously consumed tobacco from an electronic cigarette, an electronic pipe, an electronic cigar, an electronic water pipe, or an electronic vaporizer. Providing the subject with the verification of eligibility can include providing at least one of: a prescription from a physician or accredited healthcare provider, an eligibility card or code identifier, an activation code, an electronic dongle, a listing in a database, or an electronic security key fob. Determining and providing steps can be provided by a physician, nurse, pharmacists, accredited healthcare provider, an employee of a convenience or retail store, an internet or wireless based application, a service or business, a call center or phone based application, or a service or business.

In general, in one embodiment, a method of providing a verification of eligibility for use or purchase of a tobacco product includes: (1) sampling a subject's breath; (2) determining, from the subject's breath, whether the subject has previously used a tobacco product based upon results of the diagnostic test; and (3) providing the subject with a verification of eligibility for use or purchase of a tobacco product if the subject has previously used a tobacco product based on the determination from the subject's breath.

This and other embodiments can include one or more of the following features. The step of determining can include determining from a carbon monoxide breath analysis. The step of determining can include determining if the subject's breath has a reading of greater than 5 ppm CO which can indicate that the subject previously used a tobacco product. The step of determining can include determining if the subject's breath has a reading of greater than 10 ppm which can indicate that the subject previously used a tobacco product. The step of determining can include determining that the subject has consumed a tobacco product within the last 24 hours. The step of determining can include determining whether the subject has consumed a tobacco product on a regular basis, and wherein the step of providing a verification of eligibility can include providing the verification for eligibility only if the subjected has consumed tobacco products on a regular basis. The step of determining can include determining whether the subject has previously consumed combustible tobacco. The step of determining can include determining whether the subject has previously consumed tobacco from an electronic cigarette, an electronic pipe, an electronic cigar, an electronic water pipe, or an electronic vaporizer, or other non-combustion tobacco product. Providing the subject with the verification of eligibility can include providing at least one of: a prescription from a physician or accredited healthcare provider, an eligibility card or code identifier, an activation code, an electronic dongle, a listing in a database, or an electronic security key fob. Determining and providing steps can be provided by a physician, nurse, pharmacists, accredited healthcare provider, an employee of a convenience or retail store, an internet or wireless based application, a service or business, a call center or phone based application, or a service or business.

In general, in one embodiment, a method of providing a tobacco product includes: (1) determining whether a subject has previously used a tobacco product based on a diagnostic assay performed on the subject; and (2) providing a tobacco product to the subject if the diagnostic assay indicates that the subject has previously used a tobacco product.

This and other embodiments can include one or more of the following features. The step of determining can include determining at the point of sale. The step of determining can include performing the diagnostic assay using a sensor on the tobacco product. The step of determining can include performing the diagnostic assay. The step of determining can include looking up the results of the diagnostic assay in a database using a unique identifier of the subject. The tobacco product can include an electronic cigarette, an electronic pipe, an electronic cigar, an electronic water pipe, or an electronic vaporizer. The step of determining can include determining whether the subject has previously used a tobacco product based on a diagnostic test which can include a carbon monoxide breath analysis. The step of determining can include determining whether the subject has previously used a tobacco product based on a diagnostic test which can include a carbon monoxide breath analysis, wherein a reading of greater than 5 ppm CO in a breath sample can indicate that the subject has previously used a tobacco product. The step of determining can include determining whether the subject has previously used a tobacco product based on a diagnostic test which can include a saliva, blood, or urine test for nicotine, cotinine, or nicotine by-products.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3E is a table showing exemplary cut-off values for various biomarkers such that a subject's measured level of the biomarker above the cut-off value indicates eligibility for a modified risk or other tobacco product;

FIG. 4 illustrates a possible configuration of a REMS component program for the purchase of Modified Risk Products or other tobacco products;

FIG. 5 illustrates a possible configuration of a REMS component program for User Verification of a Modified Risk Product or other tobacco product;

FIG. 6 illustrates a possible configuration of a REMS component program for User Verification, Tracking, and Automated Reporting Method of a Modified Risk Product or other tobacco product and also illustrates a possible system for verification, tracking, and reporting use of, and or subject compliance for the use of a Modified Risk Product;

DETAILED DESCRIPTION OF THE INVENTION

Figure 1A:
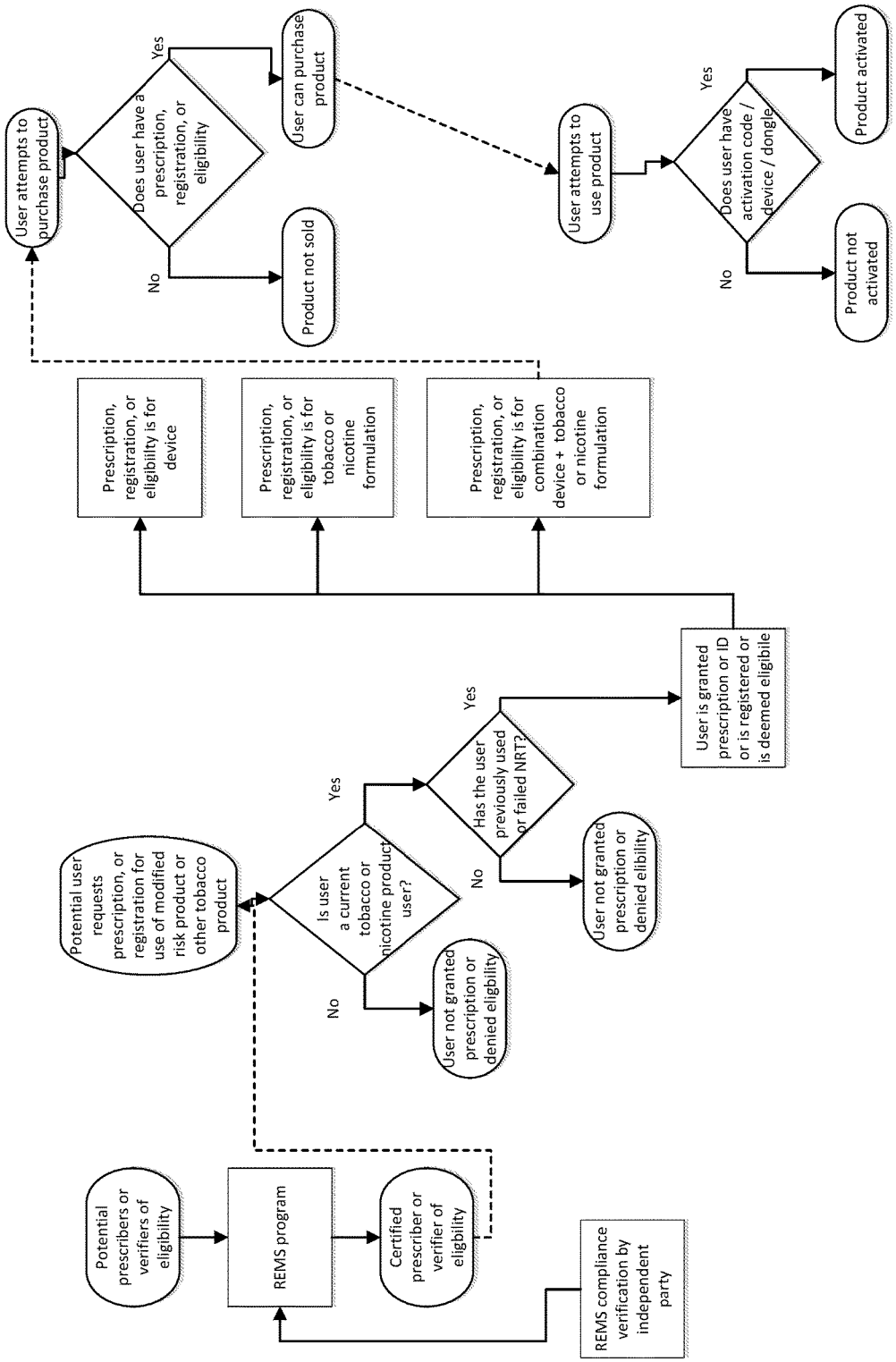
FIG. 1A illustrates a possible configuration of an overall Risk Evaluation and Mitigation Strategy (REMS) where a subject has previously used a nicotine replacement therapy.

Provided herein are methods of protecting the public health by increasing the likelihood that a subject addicted to a tobacco product will stop using a tobacco product wherein the subject has previously failed to stop using a tobacco product by other means.

It should be understood that at a minimum, terms used throughout this specification have the following meanings:

Definitions

Abstinence: Abstinence has diverse forms and several potential definitions. Commonly it refers to a temporary or partial refrain from food, alcohol, sexual activity, or drugs, such as nicotine in tobacco products. Alternately, it could be used to describe total abstinence where something is completely removed from one's lifestyle for a period of time. As it applies herein, abstinence is generally intended to have the more common meaning of temporary or partial, self-enforced, restraint from indulgence. However, the term may also imply long-term restraint, wherein a subject has maintained a sustained abstinence; i.e.: several years, without necessarily having quit using said products entirely.

Administer/Administration: Is intended to mean that a product or service has been provided to a subject. Such service may include performing a test, delivering a prescription, or carrying out/providing a verification process.

Fail/Failed/Failure: is intended to mean that a subject has not succeeded with a previous therapy and returned to previous levels (or greater levels) of tobacco product use. It is commonly understood in therapy programs that early "failure" is a normal part of trying to stop, and more than one attempt at stopping smoking prior to longer-term success is common. Alternatively it could mean inability to refrain from total or sustained abstinence.

Fail/Failed/Failure: May also mean that a subject continues to use a NRT product longer than indicated by the prescribing method or suggested use, with or without additional use of a tobacco product in addition to the NRT product. For example; a subject may continue using a nicotine patch while continuing to smoke cigarettes, beyond the intended "weaning off" period.

Initiate: Is intended to mean that a subject has at some point begun using any tobacco cessation therapy or Nicotine Replacement Therapy (NRT) product.

Modified Risk Product: Is intended to mean a tobacco product that is sold, distributed, or marketed under regulatory authority, with a claim to reduce harm or the risk of tobacco related diseases, or a tobacco product that is shown to substantially reduce the overall exposure to harmful substances.

Modified Risk Product: May also mean a tobacco or nicotine delivery device or product that is sold, distributed, or marketed under regulatory authority comprising a non-combustion-based, or vaporization-based nicotine delivery mechanism with a lower risk factor for one or more tobacco related diseases or exposure to one or more harmful substances, which may be substituted for any other oral, combustion, or vaporization-based nicotine delivery product having a higher risk factor for one or more tobacco related diseases or exposure to one or more harmful substances.

Prescribe/Prescription: Is intended to mean that a product has been authorized for distribution to a subject by order of an accredited healthcare provider (a physician); i.e.: by prescription (Rx).

Prescribe: May also mean a commonly available over-the-counter product that has been recommended by an accredited healthcare provider (a physician, a nurse, a pharmacist); i.e.: by suggestion the use an OTC product, not requiring a Rx, but still requiring verification of a type to meet local, state, or federal regulation by an accredited individual, at the point of distribution. Alternately a person may self-prescribe an available OTC product.

Quit: is intended to mean that a subject has completely stopped using a (tobacco) product; i.e.: total (i.e.: smoking) cessation.

Tobacco product: Is generally intended to mean any product produced from any genus of Nicotiana plants or nightshade family of plants, or a by-product derived therefrom, comprising nicotine, nicotine salts, or nicotine derivatives, which may produce by-products that can be ingested utilizing oral, combustion, or vaporization delivery.

Tobacco alternative: May also comprise substitute herbal tobacco products such as corn silk, mint, cinnamon, lemongrass, clover, bugasse, and shisha, among others, comprising nicotine, nicotine salts, or nicotine derivatives, which are often mixed or flavored with various fruit flavors, energy drink flavors, or other appealing flavors and which may produce byproducts that can be ingested utilizing oral, combustion, or vaporization delivery.

Treat: Is generally intended to mean providing an alternate remediation to a tobacco product to a subject. Providing a remediation to act upon a subject by providing an agent intended to be a substitute for a tobacco product.

Treat: May also mean substitution of a first tobacco product with a second tobacco product, wherein the second product has a preferable risk profile, i.e.: substitution of a tobacco product which utilizes combustion with a tobacco or nicotine product which does not utilize combustion or which utilizes vaporization.

Validate/Validation: Is intended to mean a procedure for checking that a product, service, or system has met the needs or requirements of the stakeholder(s), and is typically done in the later phases of product, process, or system development to assure that the development and verification procedures for a product, service, or system result in a product, service, or system that meets initial requirements, specifications and regulations.

Vapor/vaporize/vaporization: Is intended to mean converting a normally liquid or solid substance into an aerosol, gaseous or semi-gaseous state, where it is diffused or suspended in the air; i.e.: haze, mist, or steam. Vaporization is also defined as the process for producing a gaseous by-product that is produced from a normally liquid or solid state material, at a temperature which is below the combustion temperature of said material.

Verify/verification: Is intended to mean a procedure for checking that a product, service, or system complies with a regulation, requirement, specification, or imposed condition; e.g.: has met an initial set of requirements, specifications or regulations and typically performed in the initial or development phases of product, process, or system development.

Figure 1B:
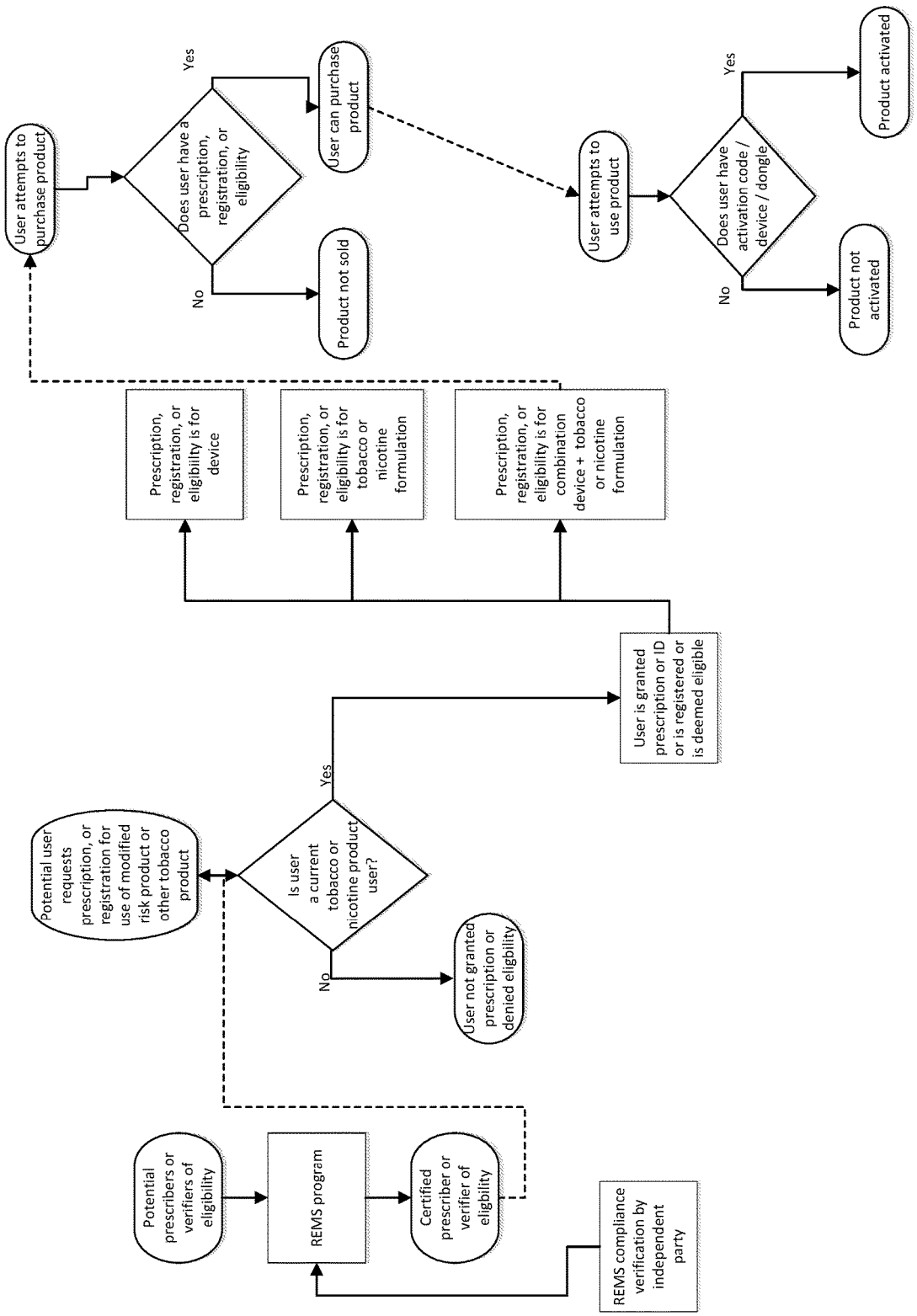
FIG. 1B illustrates another possible configuration of an overall Risk Evaluation and Mitigation Strategy (REMS) where a subject has not used a nicotine replacement therapy.

Methods:

Provided herein are methods of protecting the public health by increasing the likelihood that a subject addicted to a tobacco product will stop using a tobacco product wherein the subject has previously failed to stop using a tobacco product by other means. Such methods may include the use of controlled Risk Evaluation and Mitigation Strategies (REMS) such as that illustrated in FIGS. 1A & 1B. These REMS may be applied to drugs, biologics, devices, or combination devices that include any two or more of these things. REMS are intended to answer the question: "Do the benefits of the drug, biologic, (and/or device) outweigh the risks?" Some of the factors taken into consideration include:

Seriousness of the disease or condition to be treated
Size of the patient population;
Expected benefit of the drug or biologic (and/or device);
Expected duration of treatment;
Seriousness of the known or potential adverse events.

These evaluations are performed not only prior to the approval of a new drug, biologic, (and/or device), in this case, a modified risk product or other tobacco product device for delivering nicotine, but also throughout the entire life cycle of the drug, biologic and/or device. This serves as a means to continuously assess the safety and efficacy of existing products based on adverse event reports and results from post-marketing clinical studies.

For every drug, biologic and/or device approved by the FDA, the risks associated with its use are communicated through the product package insert. In some cases, however, the manufacturer and/or the FDA may determine that expanded REMS are necessary to go beyond product labeling in order to manage risks and thereby ensure that the benefits outweigh the risks.

Figure 2:
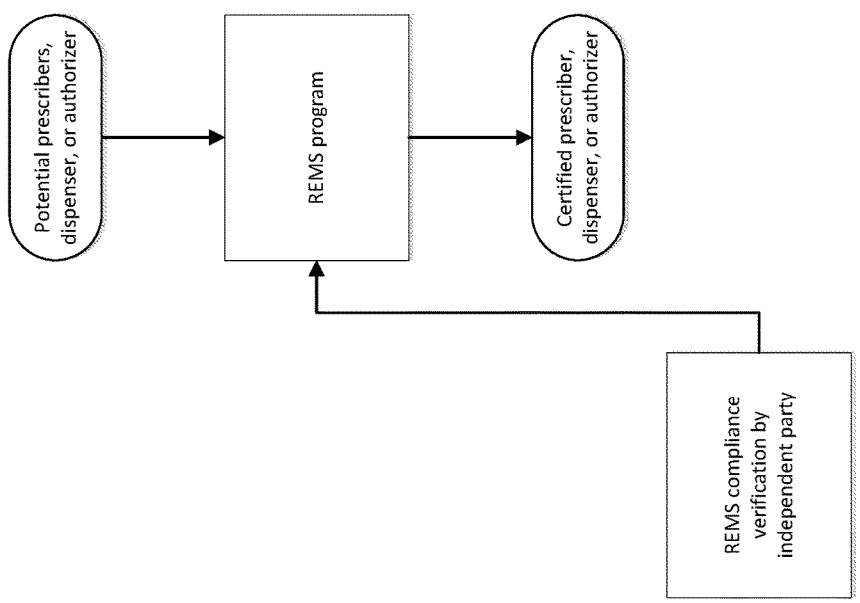
FIG. 2 illustrates a possible configuration of a REMS component program for the authorization, verification and program compliance of qualified prescribers and dispensers of modified risk products or other tobacco products.
Figure 3A:
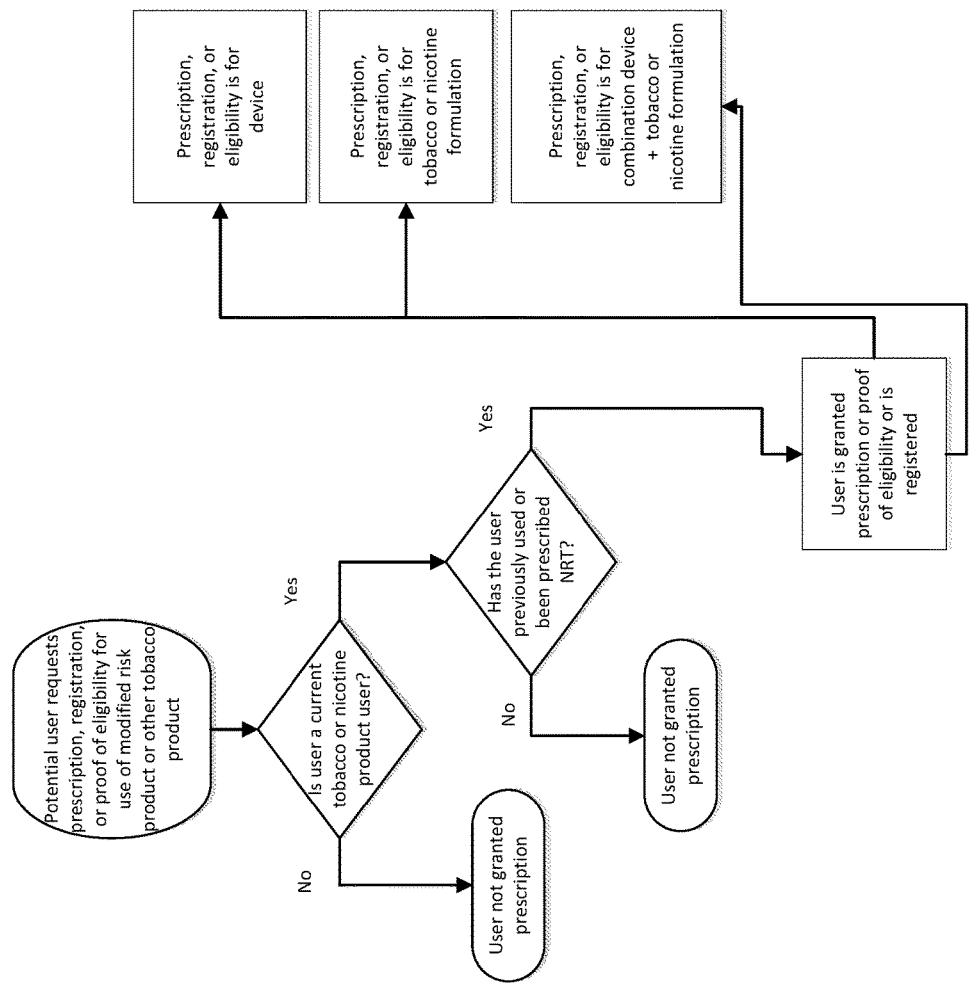
FIG. 3A illustrates a possible configuration of a REMS component program for the authorization and dispensation of prescriptions for a Modified risk product or other tobacco product or other tobacco product when a subject has previously used a nicotine replacement therapy.
Figure 3B:
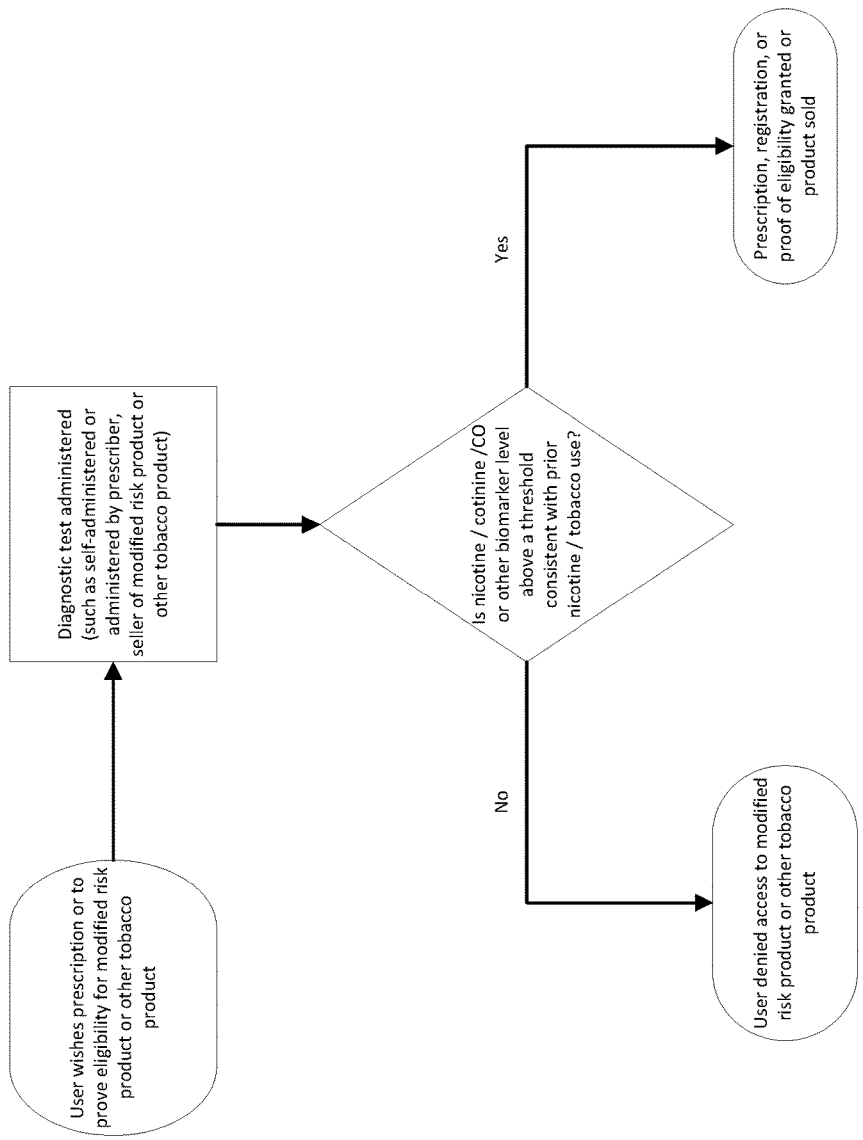
FIG. 3B illustrates a possible configuration of a REMS component program for the authorization and dispensation of prescriptions for a Modified Risk Product or other tobacco product when a subject has previously not used a nicotine replacement therapy.
Figure 3C:
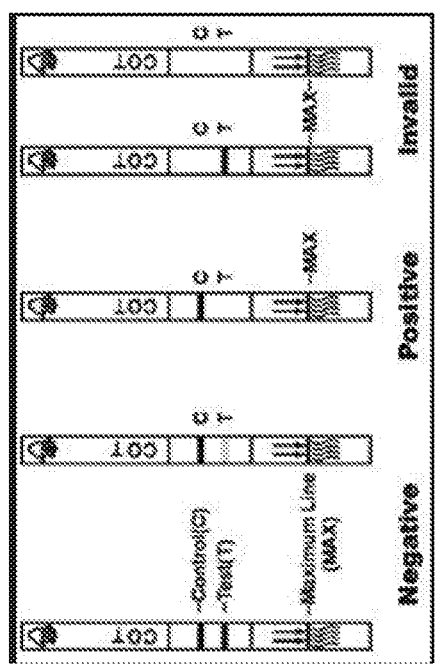
FIG. 3C illustrates a representative test strip for verification of nicotine presence in a subject's system.
Figure 3D:
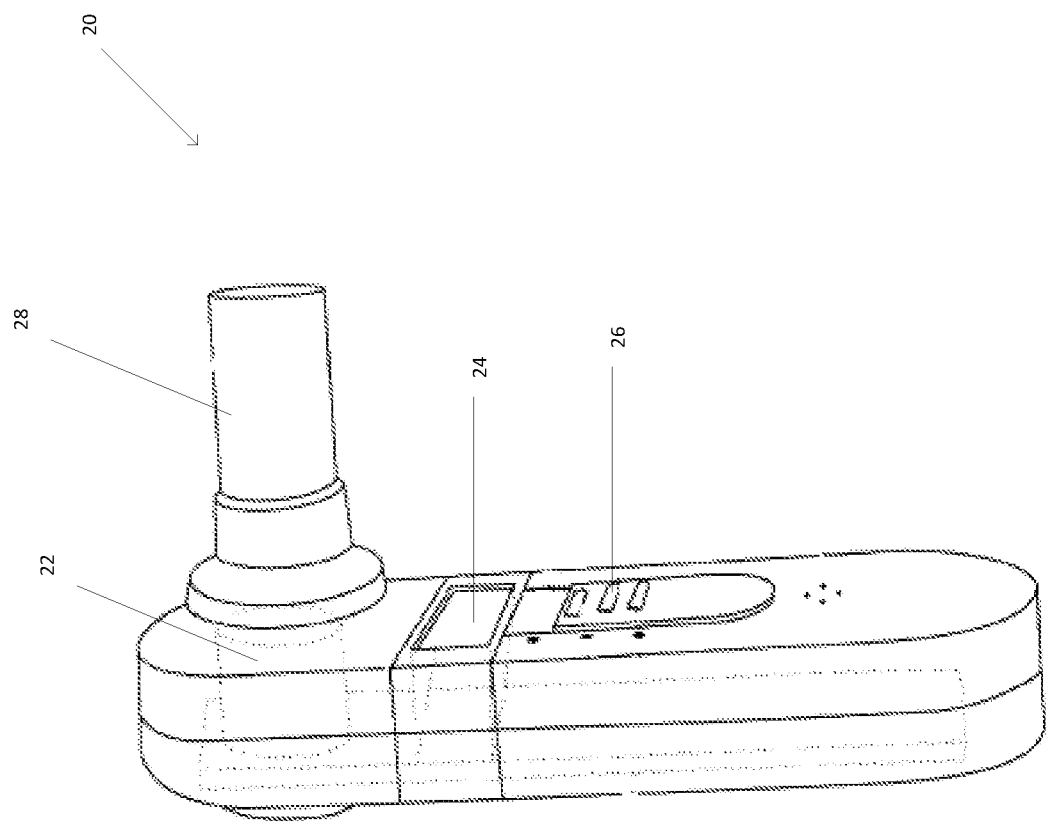
FIG. 3D illustrates an exemplary carbon monoxide monitor for verification of a subject's prior tobacco use.
Figure 7A:
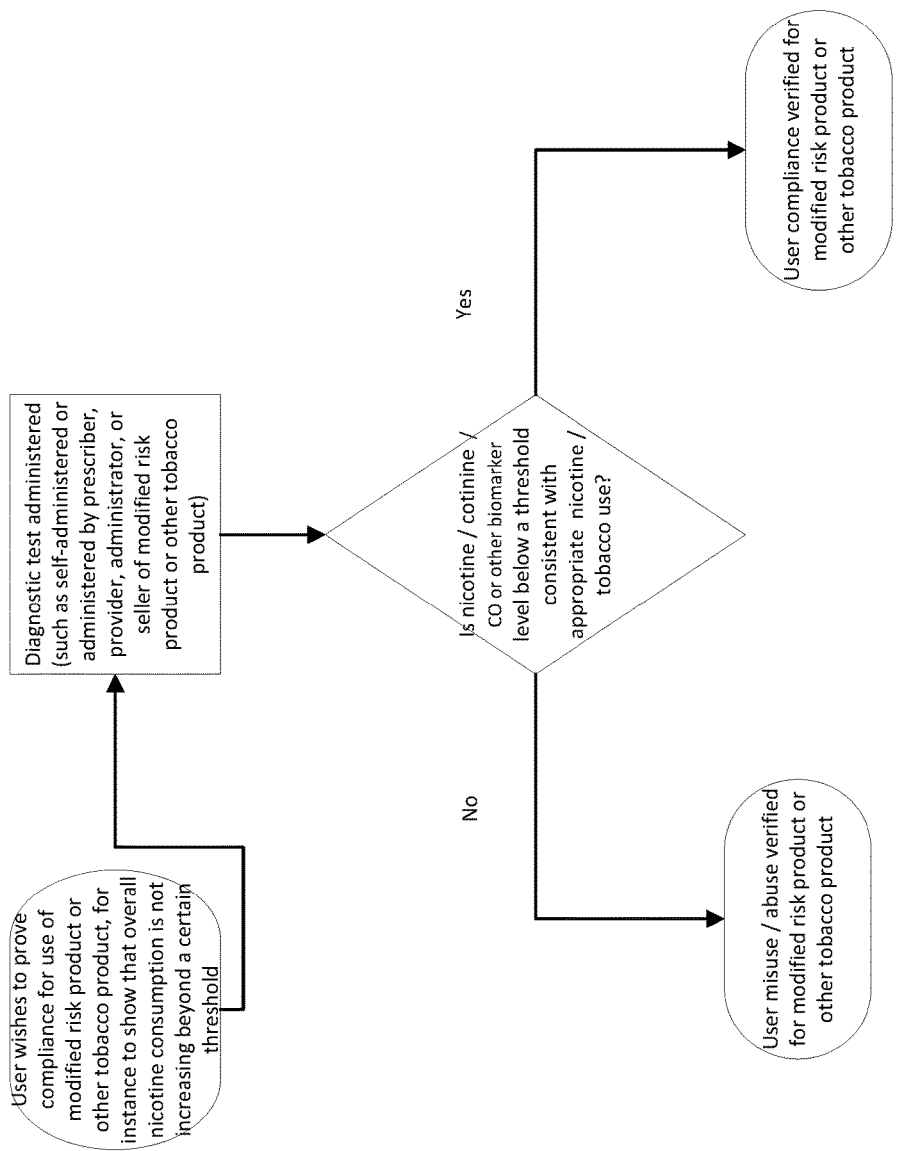
FIG. 7A illustrates a possible configuration of a REMS component program for User Eligibility for, or User Compliance of, a Modified Risk Product or other tobacco product.
Figure 7B:
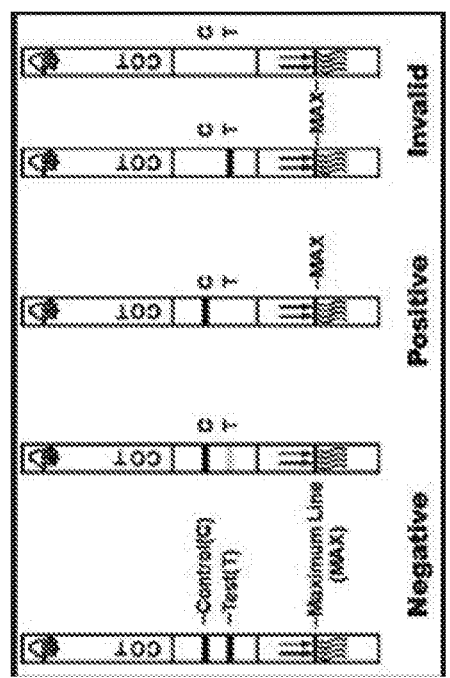
FIG. 7B illustrates a representative test strip for verification of nicotine presence in a subject's system which could be adapted for use in a REMS program for User Compliance or testing for misuse or abuse of a Modified Risk Product or other tobacco product.

As illustrated in FIGS. 1 & 2, elements of a REMS program for Nicotine Replacement Therapy (NRT) may include Elements to Assure Safe Use, (ELASU). A Nicotine REMS program as proposed herein is likely to comprise several algorithms including:

1. A Prescriber/Dispenser Authorization Algorithm (FIG. 2): which may include;
   Specific personnel authorized by statute to prescribe or dispense a Modified risk product or other tobacco product
   A defined Risk Evaluation and Mitigation Strategy for the specific Modified risk product or other tobacco product
   An auditing and certification program to verify that qualified prescribers/dispensers are appropriately trained and following the REMS protocols for verification and dispensation of Modified risk products or other tobacco products
2. A Prescription Process and Verification Algorithm (FIGS. 3A & 3B): which may include;
   A method for verifying that only qualified subjects receive a Modified risk product or other tobacco product, which may include one or more of the following:
      i. evidence of meeting a minimum age requirement;
      ii. evidence of a previously failed nicotine replacement therapy;
      iii. evidence of a at least one failed attempt by the patient to quit using such tobacco product;
      iv. collecting samples and measuring nicotine levels, nicotine levels, CO levels, or other biomarker levels in blood, expelled breath, saliva, hair, or urine to verify that the subject's nicotine or nicotine by-product levels, nicotine levels, CO levels, or other biomarker levels are above or consistent with levels expected for a tobacco or nicotine user; (FIG. 3C)
      v. a prescription from a physician or accredited healthcare provider;
      vi. electronic or telephonic verification of a unique subject eligibility card or code identifier;
      vii. software verification of a unique subject eligibility card or code identifier;
      viii. electronic fingerprint verification of an eligible subject;
      ix. an activation code;
      x. an electronic dongle; and
      xi. an electronic security key fob, or equivalent.
   A process for dispensing the Modified risk product or other tobacco product which may include;
      i. Directly providing a dispensing modified risk device and/or a modified risk tobacco/nicotine product
      ii. Registration in a REMS program
3. A User Purchasing Verification Algorithm (FIG. 4): which may include;
   A method for verifying that a qualified subject may purchase a modified risk product or other tobacco product from an authorized distributor, which may include one or more of the following:
  i. evidence of meeting a minimum age requirement;
  ii. evidence of a previously failed nicotine replacement therapy;
  iii. evidence of a at least one failed attempt by the patient to quit using such tobacco product;
  iv. collecting samples and measuring nicotine levels, nicotine levels, CO levels, or other biomarker levels in blood, expelled breath, saliva, hair, or urine to verify that the subject's nicotine or nicotine by-product levels, nicotine levels, CO levels, or other biomarker levels are above or consistent with levels expected for a tobacco or nicotine user;
  v. a prescription from a physician or accredited healthcare provider;
  vi. electronic or telephonic verification of a unique subject eligibility card or code identifier;
  vii. software verification of a unique subject eligibility card or code identifier;
  viii. electronic fingerprint verification of an eligible subject;
  ix. an activation code;
  x. an electronic dongle; and
  xi. an electronic security key fob, or equivalent.
4. A Product User Verification (FIG. 5): which may include;
  A method or process for verifying a subject is authorized to use a Modified risk product or other tobacco product before a product will be activated or function; which may include one or more of the following:
    i. software verification;
    ii. card or code identifier;
    iii. electronic fingerprint verification of an eligible subject;
    iv. lip print verification of an eligible subject;
    v. a special article of clothing;
    vi. an activation code;
    vii. an electronic ring;
    viii. an electronic dongle; and
    ix. an electronic security key fob, or equivalent.
5. A User Verification and Mitigation Tracking System (FIG. 6): which may include;
  A Modified Risk System (100) comprising: one or more of the following:
    i. an electronic cigarette; (1)
    ii. an electronic pipe;
    iii. an electronic cigar;
    iv. an electronic water pipe; or
    v. an electronic vaporizer (1), and also comprising one or more of the following:
      1. a battery, an atomizer or cartomizer, electronic circuitry, a memory storage device for tracking component usage activity, a means of memory transfer, and a charging circuit;
    vi. a charger base station (2) comprising one or more of the following:
      1. a memory storage device; a means for receiving data and transmitting said data from said modified risk product or other tobacco product memory storage device to a third party;
    vii. an identification recognition system;
    viii. activation software for recognition of a specific device keyed to said charger base and capable of interfacing with an external device, wherein said external device comprises one or more of the following:
      ix. a smart phone (3); a computer; an electronic fob (4); an electronic dongle;
    a ring; an article of clothing; and a wireless communication device (5).
6. A REMS Compliance Program (FIG. 7A): which may include;
  A method of testing to confirm that a subject is complying with (and not misusing or abusing) the Modified risk product or other tobacco product.
    i. Testing strips, CO level, or other methods of compliance verification (FIGS. 7B and 3D).

Described herein are methods of: (1) increasing the likelihood that a subject will stop using a tobacco product or tobacco alternative; and (2) decreasing the likelihood that a subject not using a tobacco product will start using the tobacco product. The methods include providing a modified risk product or other tobacco product, such as a device for administration of nicotine in a vapor form, if the subject: (1) has previously failed a nicotine replacement therapy; (2) had a failed attempt to quit using the tobacco product; (3) has a prescription or other verification mechanism indicating eligibility for purchase or use of the modified risk product or other tobacco product.

Provided herein is a method of protecting public health comprising: increasing the likelihood that a first subject or a second subject will stop using a tobacco product or tobacco alternative product by providing a modified risk product or other tobacco product such as a device for administration of nicotine in a vapor form to a first subject addicted to the tobacco product wherein the first subject has previously failed a nicotine replacement therapy. It is generally understood that there are numerous recognized therapies intended to reduce the use of tobacco and/or bring about the cessation of addiction to tobacco products and in particular, nicotine. These include; abstinence, nicotine gum, nicotine oral spray, nicotine inhaler, nicotine nasal spray, nicotine lozenge, nicotine dermal patch, Bupropion®, Chantix®, or similar medications and oral nicotine replacement products. In many cases, these products or methods fail. The applicant believes that by combining a REMS program with their Modified risk product or other tobacco product, the user will be more likely to switch to a preferred form of nicotine delivery which has a preferable risk profile, while also minimizing the risk that non-tobacco users will initiate use of the modified risk product or other tobacco product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a REMS typically involving one or more of the following components; subject eligibility verification, subject compliance verification to a risk mitigation strategy, and overall validation of the success of said risk evaluation and mitigation strategy.

Among the methods included in the REMS are methods wherein the product is prescribed, provided, or a subject's eligibility is verified by a physician, a nurse, a pharmacist, or an accredited healthcare provider. FIG. 3A illustrates one embodiment of a method wherein the potential subject may request a prescription for a controlled product from a qualified, accredited healthcare provider, who verifies that the subject is qualified to receive said product, prior to issuing a prescription. A subject may be a current tobacco or nicotine user who may have previously tried and failed a nicotine replacement therapy.

Alternatively, the product may be regulated as an over the counter (OTC) or retail product, wherein the subject may self-subscribe and acquire the product by personally requesting it from a qualified individual, authorized to dispense said product, upon proof or verification of eligibility to acquire said product, such as proof of a minimum age requirement, etc. FIG. 3B illustrates another embodiment of a method wherein the potential subject may request an FDA designated modified risk tobacco product or a tobacco alternative product which may include a non-combustion or vaporization-based delivery of nicotine or tobacco from a qualified, accredited healthcare provider, or employee of a convenience or retail store, who verifies that the subject is qualified to receive said product. A subject may be a current tobacco or nicotine user who may or may not have previously tried and failed a nicotine replacement therapy. A simple nicotine test strip may be all that is required for this verification. Alternately, verification may require more complex tests comprising: blood, expelled breath, hair, or urine taken for analysis.

In some embodiments, the devices and methods of using the modified risk product or other tobacco product may be provided by, or subject eligibility verified by, an accredited employee of a convenience or retail store or by an employee of an accredited convenience or retail store.

In still other situations, the product is prescribed, provided, and or subject eligibility verified by an internet or wireless based application, service or business. While in still other situations the product may be prescribed, provided, or subject eligibility verified by a call center or phone based application service or business. The use of Skype or other real time phone and internet services makes these verification and prescribing services possible.

In any of the preceding examples, the prescribers or providers of the modified risk product or other tobacco product have been qualified to deliver said modified risk product or other tobacco product through a REMS compliance verification program as illustrated in FIG. 2, which is typically administered and controlled by a qualified independent party having full authorization to qualify said providers and/or their employees and to audit their internal systems for recordkeeping. Either the facility employing the prescribers or providers or the individual prescribers or providers themselves may be qualified and audited.

In some embodiments, the subject eligibility verification comprises providing a prescription from an accredited healthcare provider, verifying a subject's identity, a minimum age for eligibility, or verification of a prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product or other tobacco product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the risk evaluation and mitigation strategy (REMS) may incorporate a means of subject compliance verification and or the subject's eligibility to participate in a REMS program and have a modified risk product or other tobacco product prescription. Subject compliance is commonly used in clinical drug studies to verify the concentration levels and patient compliance to protocols, among other clinical study outcome measures. FIG. 7 illustrates one possible configuration for such a REMS program wherein a subject's eligibility to participate in a program is first verified prior to being given a prescription, and the subject may be tested again at a later date to demonstrate program compliance.

In other embodiments, the compliance verification or the REMS program validation may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine or tobacco products in the market.

Some aspects of these methods may require physical tests that must be performed to provide accurate and quantifiable data wherein the subject must present themselves to a qualified individual in order for the test to be completed. In some embodiments, the subject compliance verification or the REMS program validation testing is performed by a physician, a nurse, a pharmacist, a phlebotomist, or an accredited healthcare provider and the samples obtained are sent to a qualified lab for analysis.

In other embodiments, subject compliance verification is performed by an accredited employee of a convenience or retail store, or an employee of an accredited convenience or retail store. Such compliance tests would comprise verification of subject identity and collection of saliva, hair, urine, or breath samples, which could be forwarded to a qualified lab for analysis.

Alternatively, subject compliance or the REMS program validation may be measured passively through the use of electronic technology. One such example of this is illustrated in FIG. 6. In this example, a device that is a component of modified risk system, may comprise an electronic cigarette, an electronic pipe, an electronic cigar, an electronic water pipe, or an electronic vaporizer for delivering a nicotine-containing vapor, comprising a battery, an atomizer, electronic circuitry, a memory storage device for tracking components of usage activity, a means of memory transfer, and a charging circuit, along with a charger base station comprising a memory storage device, a means for receiving data from said component device memory storage device and then having the ability to transmit said data to a third party which passively monitors the device and indirectly, the subject for compliance based on the transmitted data.

The component device and the charging base would be configured such that activation software would be required for recognition of the specific device, keyed to said charger base. This software could be embedded and matched to each component set in a modified risk product or other tobacco product, and be capable of interfacing with an external device, wherein said external device comprises; a smart phone, computer, electronic fob, electronic dongle and a Bluetooth or wireless communication device, which would need to be within a fixed range for activation and continued use.

Alternatively, the components could be configured with a programmable code which must be entered periodically for activation. Still further the components could be hard wired with a timing circuit that requires periodic physical contact between the components for activation.

In addition, the transmission of collected data could occur over the internet via a hardwired or wireless connection through a base computer device for analysis and validation by an accredited healthcare professional or REMS monitor or administrator.

Provided herein is a method of protecting public health comprising: increasing the likelihood that a first subject or a second subject will stop using a tobacco product by providing a modified risk product or other tobacco product for administration to the first subject addicted to the tobacco product only after at least one failed attempt by the first subject to quit using such tobacco product. These modified risk products or other tobacco products comprise an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

The previously failed attempt to quit using a tobacco product commonly comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments of the method, the product is prescribed, provided, administered, or a subject's eligibility is verified by a physician, a nurse, a pharmacist, or an accredited healthcare provider, as illustrated in FIG. 3.

In other embodiments, the product, which may be an OTC product, is provided, administered, or subject eligibility verified by an accredited employee of a convenience or retail store. In still other embodiments, the product is provided, administered, or a subject's eligibility is verified by an employee of an accredited convenience or retail store.

In still other embodiments, the product which may be either a prescription or OTC product, is provided, administered, or a subject's eligibility is verified by an internet or wireless based application, service or business. In still other embodiments of the method the product is provided, administered, or a subject's eligibility is verified by a call center or phone based application service or business, using Skype or other real time phone and internet services.

In some embodiments, the subject eligibility verification comprises providing a prescription from an accredited healthcare provider, verifying a subject's identity, a minimum age for eligibility, or verification of a prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user.

In some embodiments, the risk evaluation and mitigation strategy incorporates a means of subject compliance verification.

In some embodiments, the subject compliance verification comprises collecting and sending samples taken before (and/or in some variations, after) being provided a modified risk product or other tobacco product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require physical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider.

In other embodiments, subject compliance verification is performed by an accredited employee of a convenience or retail store, or an employee of an accredited convenience or retail store.

Provided herein is a method of protecting public health comprising increasing the likelihood that a first subject or a second subject will stop using a tobacco product by providing a modified risk product or other tobacco product for administration to the first subject addicted to the tobacco product, only after the modified risk product or other tobacco product is prescribed to the first subject or the first subject is otherwise verified as eligible to purchase or use the product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the product is prescribed by a physician, a nurse, a pharmacist, or an accredited healthcare provider.

In some embodiments, the subject eligibility verification comprises providing a prescription from an accredited healthcare provider, verifying a subject's identity, a minimum age for eligibility, or verification of a prior nicotine replacement therapy.

Referring to FIG. 3B, in some embodiments, the subject eligibility verification includes administering a diagnostic test. For example, the diagnostic test can include collecting samples and measuring nicotine or other by-product of tobacco use, such as cotinine, levels in blood samples, expelled breath samples, saliva samples, hair samples, and in urine samples to verify that the subject's nicotine or nicotine by-product levels are above or consistent with levels expected for a tobacco or nicotine user. As shown in FIG. 3C, a nicotine or cotinine test can determine whether the subject is positive or negative for tobacco. In some embodiments, a cotinine concentration of greater than 7 ng/ml, greater than 8 ng/ml, greater than 10 ng/ml, or greater than 12 ng/ml in a subject's saliva can be used to identify a user of tobacco. Likewise, a cotinine concentration of greater than 35 ng/mL, greater than 40 ng/mL, greater than 42 ng/mL, or greater than 49 ng/mL in a subject's urine can be used to identify a user of tobacco.

Another example of a diagnostic test for subject eligibility verification is a breath carbon monoxide (CO) test. The breath carbon monoxide test can be administered, for example, with a carbon monoxide breath monitor 20 as shown in FIG. 3D. In some embodiments, the monitor can be handheld. The carbon monoxide monitor 20 can include a sensor 22, such as an electrochemical gas sensor, and a mouthpiece 28 for the subject to expel air through. The sensor 22 can be used to detect the carbon monoxide in parts per million (ppm). In some embodiments, a CO concentration of greater than 5 ppm, greater than 6 ppm, greater than 8 ppm, or greater than 10 ppm can be used to identify a user of tobacco, e.g. a user of combustible tobacco. For example, the minimum threshold level can be between 3-5 ppm, between 5-10 ppm, or greater than 10 ppm. In some embodiments, the CO level in a user's blood can be used to determine whether the user has ingested tobacco. The carbon monoxide test can advantageously detect CO when someone ingested tobacco within 10 hours before the test, such as within 8 hours or within 6 hours. Likewise, the carbon monoxide test can detect when someone has ingested tobacco regularly such that CO has built up a reservoir in their blood or lungs. In some embodiments, the carbon monoxide test can be given in the morning (such as within 4 hours of the subject awaking), as regular tobacco users tend to use tobacco within several hours of waking. Further, the carbon monoxide test can be used to determine whether the subject is a light or heavy smoker. For example, a reading of between 6 and 10 ppm can indicate a light user, and a reading of greater than 10 ppm can indicate a heavy user. In some embodiments, eligibility verification can be provided only for heavy users.

Any of the diagnostic tests described herein can also include a mechanism to exclude or select for users who have particular smoking, cardiovascular, or respiratory diseases or conditions, such as asthma or chronic obstructive pulmonary disease (i.e., the eligibility verification can be negative such that the user cannot obtain the modified risk product). For example, the diagnostic test can include a nitric oxide (NO) breath analysis to eliminate or select for these subjects.

It is to be understand that additional diagnostic tests can also be used to determine if the subject is a tobacco user, such as tests for thiocyanate, 4-Aminobiphenyl-hemoglobin adduct, Benzo[a]pyrene-DNA adduct, PAH-albumin adduct, urinary tobacco-specific nitrosoamines, urine hyroxyproline, and/or urine mutagenicity levels in the subject. Exemplary cut-off levels for various diagnostic tests (i.e. a measured level above the cut-off value indicates a tobacco user eligible for use of the modified risk product) are included in FIG. 3E.

In some embodiments, when a diagnostic test is used to determine eligibility verification, the readings can be displayed on the device itself. For example, the specific readings (e.g., ppm of CO) can be indicated on a display of the device, such as the display 24 of device 20 or an indication of passing the cut-off value (e.g., a particular light 26 or the word "pass" on the display 24 of the device 20) can be indicated on the monitor or device. In other embodiments, when a diagnostic test is used, the results can be processed by a third party, e.g., the device or readings from the device can be passed onto a third party to determine whether the subject is eligible for the modified risk product.

Once the subject is verified as eligible (e.g., based upon the results of the diagnostic test or prescription by a physician or healthcare provider), the verified subject can be provided with evidence of eligibility for purchase or use of the modified risk product. For example, subject may be provided with an electronic or telephonic verification of a unique subject eligibility card or code identifier, software verification of a unique subject eligibility card or code identifier, electronic fingerprint verification, an activation code, entry into a database, or an electronic dongle, electronic security key fob, or the equivalent.

In some embodiments, components of the subject eligibility verification may be performed by a physician, a nurse, a pharmacist, an accredited healthcare provider, or an employee of a convenience or retail store. In some embodiments, components of the subject eligibility verification can be self-administered.

In some embodiments, the risk evaluation and mitigation strategy incorporates a means of subject compliance verification. In some embodiments, the subject compliance verification comprises collecting and sending samples taken before (and/or in some variations, after) being provided a modified risk product, for analysis to an accredited testing facility, and measuring the difference between samples for nicotine levels in blood, expelled breath, saliva, hair, and in urine. In some embodiments, components of the subject compliance verification may be performed by a physician, a nurse, a pharmacist, an accredited healthcare provider, or an employee of a convenience or retail store. In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette. In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require phyisical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider. In other embodiments, subject compliance verification is performed by an employee of a convenience or retail store.

Referring to FIG. 5, in some embodiments, the device itself can include a diagnostic test for verification eligibility. For example, the modified risk product or other tobacco product can include a CO breath analysis sensor directly on the device, such as on the mouthpiece of the modified risk product, that only allows use of the device if the user is verified as a user of tobacco (e.g. has a CO level of above a particular amount as described above, including above average values for a non-tobacco user).

Examples of sensors and sensor technologies that may be used may include electrochemical and Metal oxide semiconductor (MOS) sensors. An electrochemical sensor may produce a current that is related to the target gas concentration around a sensor. For example, an electrochemical cell may be used, to provide a highly accurate and linear output to carbon monoxide concentration, requiring minimal power, and has a long lifetime (e.g., 5 years or greater). MOS (Metal oxide semiconductor) are typically low cost, small size and may provide superior performance. For example, the Figaro TGS5342 electrochemical sensor is 15 mm diameter, 27.9 mm length, however similar sensors may be smaller. In particular, sensors configured to operate as a gating/enabling tool for use of any of the devices (e.g., modified risk products or other tobacco products) described herein may be specifically adapted to sample a patient's breath before they can operate the device. Once the sensor has confirmed that the CO level is above a naïve threshold (e.g., a threshold of CO levels for non-smokers, and/or those who have not used modified risk products or other tobacco products before), the device may be enabled for operation for some amount of time (e.g., seconds, minutes, hours). Other examples of sensors may include SGX sesnortech (E.g., EC4-2000-CO and MICS-4514 MOS sensors), Figaro TGS3870 MOS sensors, and the like.

Provided herein is a method of protecting public health comprising decreasing the likelihood that a second subject not using a tobacco product will start using the tobacco product by providing a modified risk product or other tobacco product for administration to the first subject addicted to the tobacco product wherein the first subject has previously failed nicotine replacement therapy.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy. In some embodiments, the previously failed attempt to quit using said tobacco product comprises abstinence, nicotine gum, nicotine oral spray, nicotine inhaler, nicotine nasal spray, nicotine lozenge, nicotine dermal patch, Bupropion, Chantix, or comparable oral nicotine replacement product.

In some embodiments, the product is prescribed by a physician, a nurse, a pharmacist, or an accredited healthcare provider.

In some embodiments, the subject eligibility verification comprises providing a prescription from an accredited healthcare provider, verifying a subject's identity, a minimum age for eligibility, and/or verification of a previously failed prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user.

One such mitigation strategy is illustrated in FIG. 4. As illustrated herein, the subject attempting to purchase or acquire a controlled modified risk product or other tobacco product would provide some form of qualified proof that verifies they are qualified to obtain said Modified risk product or other tobacco product and participate in the REMS. This purchase verification requirement would typically comprises, a prescription for a controlled substance in addition to a formal verification of subject identity which may comprise a fingerprint, facial recognition, retinal scan, or other biometric identification. Alternatively the identification and verification may comprise having the subject providing a code, a dongle, an electronic FOB, or web registration, to name but a few methods.

In some embodiments, the product is provided or a subject's eligibility is verified by a physician, a nurse, a pharmacist, an accredited healthcare provider, an accredited employee of a convenience or retail store, or an employee of an accredited convenience or retail store.

In some embodiments, the product is prescribed, provided, or subject eligibility verified by an internet or wireless based application, service or business, or by a call center or phone based application service or business. The use of Skype or other real time phone and internet services makes these verification and prescribing services possible.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require physical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider.

In other embodiments, subject compliance verification is performed by an accredited employee of a convenience or retail store, or an employee of an accredited convenience or retail store.

Provided herein is a method of protecting public health comprising decreasing the likelihood that a second subject not using a tobacco product will start using the tobacco product by providing a modified risk product or other tobacco product for administration to the first subject addicted to the tobacco product only after at least one failed attempt by the first subject to quit using such tobacco product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, and overall validation of the success of said risk evaluation and mitigation strategy.

In some embodiments, the previously failed attempt to quit using said tobacco product comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided, or subject eligibility verified by a physician, a nurse, a pharmacist, an accredited healthcare provider, an accredited employee of a convenience or retail store, or by an employee of an accredited convenience or retail store.

In some embodiments, the product is prescribed, provided, or subject eligibility verified by an internet or wireless based application, service or business, or by a call center or phone based application service or business. The use of Skype or other real time phone and internet services makes these verification and prescribing services possible.

In other embodiments, the product, which may be an OTC product, is provided, administered, or a subject's eligibility is verified by an accredited employee of a convenience or retail store, or by an employee of an accredited convenience or retail store.

In still other embodiments, the product which may be either a prescription or OTC product, is provided, administered, or a subject's eligibility is verified by an internet or wireless based application, service or business, or by a call center or phone based application service or business, using Skype or other real time phone and internet services.

In some embodiments, the subject eligibility verification comprises providing a prescription from an accredited healthcare provider, verifying a subject's identity, a minimum age for eligibility, or verification of a prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user. If a second subject has not been using a tobacco product or alternative tobacco product comprising nicotine, such samples would be negative and disqualify said second subject from obtaining a modified risk under this criteria.

As previously described, another method of decreasing the likelihood that a second subject not using a tobacco product, will start using the tobacco product after a first addicted subject is prescribed a modified use product after a previously failed attempt to quit, could comprise the passive use of electronic technology. One such example of this is illustrated in FIG. 5. In this example, a device that is a component of a modified risk system, may comprise an electronic cigarette, an electronic pipe, an electronic cigar, an electronic water pipe, an electronic vaporizer, and/or a tobacco or nicotine product, for delivering a nicotine-containing vapor, comprising a battery, an atomizer, electronic circuitry, a memory storage device for tracking various aspects of component usage activity, a means of memory transfer, and a charging circuit, along with a charger base station comprising a memory storage device, a means for receiving data from said component device memory storage device and comprising the means to transmit said data to a third party which passively monitors the device and indirectly, the subject, for compliance to the REMS based on the transmitted data.

The component device would be configured such that activation software acting as a user identification system would be required for recognition of the specific device, keyed to said charger base. This software could be embedded and matched to each component set in a modified risk product, and be capable of interfacing with an external device, wherein said external device comprises; a smart phone, computer, electronic fob, electronic dongle, a special ring, and/or a Bluetooth or wireless device, which would need to be within a fixed range for activation and continued use.

Alternatively, the device could be configured to have a fingerprint or lip print reader on the body or mouthpiece that is matched to the first subject.

Alternatively a special ring or wrist band worn on the hand of the first subject or other article of jewelry could provide a user identification system and be configured to mate with the device, wherein the device will only activate if it is in the immediate proximity of the subject's hand.

In any of the prior examples, the devices could be configured with proximity sensors requiring the subject to be within a fixed distance such as 20 feet, or ten feet, or more preferably within five feet or less.

Alternatively, the components could be configured with a programmable code which must be entered periodically for activation. Still further the components could be hard wired with a timing circuit that requires a minimal period of time between uses for activation.

In addition, the device could be configured as shown in FIG. 6 with a base having hardware and software for the transmission of collected data as previously described. In this example, the modified risk product or other tobacco product configuration could be used for user verification, user compliance, or even validation of a REMS for a modified risk product.

Provided herein is a method of protecting public health comprising decreasing the likelihood that that a subject not using a tobacco product will start using the product by providing a modified risk product or other tobacco product for administration to the first subject addicted to the tobacco product, only after the modified risk product or other tobacco product is prescribed to the first subject or the first subject is otherwise verified as eligible to purchase or use the product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the product is prescribed by a physician, a nurse, a pharmacist, or an accredited healthcare provider.

In some embodiments, the subject eligibility verification comprises providing a prescription from an accredited healthcare provider, verifying a subject's identity, a minimum age for eligibility, or verification of a prior nicotine replacement therapy.

Once the subject is verified as eligible (e.g., based upon the results of the diagnostic test or prescription by a physician or healthcare provider), the verified subject can be provided with evidence of eligibility for purchase or use of the modified risk product. For example, subject may be provided with an electronic or telephonic verification of a unique subject eligibility card or code identifier, software verification of a unique subject eligibility card or code identifier, electronic fingerprint verification, an activation code, entry into a database, or an electronic dongle, electronic security key fob, or the equivalent.

In some embodiments, components of the subject eligibility verification may be performed by a physician, a nurse, a pharmacist, an accredited healthcare provider, or an employee of a convenience or retail store. In some embodiments, components of the subject eligibility verification can be self-administered.

Referring to FIG. 3B, in some embodiments, the subject eligibility verification includes administering a diagnostic test. For example, the diagnostic test can include collecting samples and measuring nicotine or other by-product of tobacco use, such as cotinine, levels in blood samples, expelled breath samples, saliva samples, hair samples, and in urine samples to verify that the subject's nicotine or nicotine by-product levels are above or consistent with levels expected for a tobacco or nicotine user. As shown in FIG. 3C, a nicotine or cotinine test can determine whether the subject is positive or negative for tobacco. In some embodiments, a cotinine concentration of greater than 7 ng/ml, greater than 8 ng/ml, greater than 10 ng/ml, or greater than 12 ng/ml in a subject's saliva can be used to identify a user of tobacco. Likewise, a cotinine concentration of greater than 35 ng/mL, greater than 40 ng/mL, greater than 42 ng/mL, or greater than 49 ng/mL in a subject's urine can be used to identify a user of tobacco.

Another example of a diagnostic test for subject eligibility verification is a breath carbon monoxide (CO) test. The breath carbon monoxide test can be administered, for example, with a carbon monoxide breath monitor 20 as shown in FIG. 3D. In some embodiments, the monitor can be handheld. The carbon monoxide monitor 20 can include a sensor 22, such as an electrochemical gas sensor, and a mouthpiece 28 for the subject to expel air through. The sensor 22 can be used to detect the carbon monoxide in parts per million (ppm). In some embodiments, a CO concentration of greater than 5 ppm, greater than 6 ppm, greater than 8 ppm, or greater than 10 ppm can be used to identify a user of tobacco, e.g. a user of combustible tobacco. For example, the minimum threshold level can be between 3-5 ppm, between 5-10 ppm, or greater than 10 ppm. In some embodiments, the CO level in a user's blood can be used to determine whether the user has ingested tobacco. The carbon monoxide test can advantageously detect CO when someone ingested tobacco within 10 hours before the test, such as within 8 hours or within 6 hours. Likewise, the carbon monoxide test can detect when someone has ingested tobacco regularly such that CO has built up a reservoir in their blood or lungs. In some embodiments, the carbon monoxide test can be given in the morning (such as within 4 hours of the subject awaking), as regular tobacco users tend to use tobacco within several hours of waking. Further, the carbon monoxide test can be used to determine whether the subject is a light or heavy smoker. For example, a reading of between 6 and 10 ppm can indicate a light user, and a reading of greater than 10 ppm can indicate a heavy user. In some embodiments, eligibility verification can be provided only for heavy users.

Any of the diagnostic tests described herein can also include a mechanism to exclude or select for users who have particular smoking, cardiovascular, or respiratory diseases or conditions, such as asthma or chronic obstructive pulmonary disease (i.e., the eligibility verification can be negative such that the user cannot obtain the modified risk product). For example, the diagnostic test can include a nitric oxide (NO) breath analysis to eliminate or select for these subjects.

It is to be understand that additional diagnostic tests can also be used to determine if the subject is a tobacco user, such as tests for thiocyanate, 4-Aminobiphenyl-hemoglobin adduct, Benzo[a]pyrene-DNA adduct, PAH-albumin adduct, urinary tobacco-specific nitrosoamines, urine hyroxyproline, and/or urine mutagenicity levels in the subject. Exemplary cut-off levels for various diagnostic tests (i.e. a measured level above the cut-off value indicates a tobacco user eligible for use of the modified risk product) are included in FIG. 3E.

In some embodiments, when a diagnostic test is used to determine eligibility verification, the readings can be displayed on the device itself. For example, the specific readings (e.g., ppm of CO) can be indicated on a display of the device, such as the display 24 of device 20 or an indication of passing the cut-off value (e.g., a particular light 26 or the word "pass" on the display 24 of the device 20) can be indicated on the monitor or device. In other embodiments, when a diagnostic test is used, the results can be processed by a third party, e.g., the device or readings from the device can be passed onto a third party to determine whether the subject is eligible for the modified risk product.

In some embodiments, the product is administered by physician, a nurse, a pharmacist, an accredited healthcare provider, or an employee of a convenience or retail store.

In some embodiments, the product is administered by an internet or wireless based application, service or business, or by a call center or phone based application service or business. The use of Skype or other real time phone and internet services makes these verification and prescribing services possible In some embodiments, the risk evaluation and mitigation strategy incorporates a means of subject compliance verification.

In some embodiments, the subject compliance verification comprises collecting and sending samples for analysis, taken before (and/or in some variations, after) being provided a modified risk product, and measuring the difference between samples for nicotine levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require physical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider.

In other embodiments, subject compliance verification is performed by an accredited employee of a convenience or retail store, or an employee of an accredited convenience or retail store.

In some embodiments, the risk evaluation and mitigation strategy incorporates a passive means of subject compliance verification.

As previously described, a device that is a component of a modified risk system, may comprise an electronic cigarette, an electronic pipe, an electronic cigar, an electronic water pipe, an electronic vaporizer, and/or a tobacco or nicotine product, for delivering a nicotine-containing vapor, comprising a battery, an atomizer, electronic circuitry, a memory storage device for tracking various aspects of component usage activity, a means of memory transfer, and a charging circuit, along with a charger base station comprising a memory storage device, a means for receiving data from said component device memory storage device and comprising the means to transmit said data to a third party which monitors the device and indirectly, the subject, for compliance to the REMS based on the transmitted data.

The component device would be configured such that activation software acting as a user identification system would be required for recognition of the specific device, keyed to said charger base. This software could be embedded and matched to each component set in a modified risk product, and be capable of interfacing with an external device, wherein said external device comprises; a smart phone, computer, electronic fob, electronic dongle, and a Bluetooth or wireless device, which would need to be within a fixed range for activation and continued use.

Alternatively, the device could be configured to have a fingerprint or lip print reader on the body or mouthpiece that is matched to the first subject.

Alternatively a special ring or wrist band worn on the hand of the first subject or other article of jewelry or clothing could provide a user identification system and be configured to mate with the device, wherein the device will only activate if it is in the immediate proximity of the subject's hand or the subject.

Referring to FIG. 5, in some embodiments, the device itself can include a diagnostic test for verification eligibility. For example, the modified risk product or other tobacco product can include a CO breath analysis sensor directly on the device, such as on the mouthpiece of the modified risk product, that only allows use of the device if the user is verified as a user of tobacco (e.g. has a CO level of above a particular amount as described above, including above average values for a non-tobacco user).

Examples of sensors and sensor technologies that may be used may include electrochemical and Metal oxide semiconductor (MOS) sensors. An electrochemical sensor may produce a current that is related to the target gas concentration around a sensor. For example, an electrochemical cell may be used, to provide a highly accurate and linear output to carbon monoxide concentration, requiring minimal power, and has a long lifetime (e.g., 5 years or greater). MOS (Metal oxide semiconductor) are typically low cost, small size and may provide superior performance. For example, the Figaro TGS5342 electrochemical sensor is 15 mm diameter, 27.9 mm length, however similar sensors may be smaller. In particular, sensors configured to operate as a gating/enabling tool for use of any of the devices (e.g., modified risk products or other tobacco products) described herein may be specifically adapted to sample a patient's breath before they can operate the device. Once the sensor has confirmed that the CO level is above a naïve threshold (e.g., a threshold of CO levels for non-smokers, and/or those who have not used modified risk products or other tobacco products before), the device may be enabled for operation for some amount of time (e.g., seconds, minutes, hours). Other examples of sensors may include SGX sesnortech (E.g., EC4-2000-CO and MICS-4514 MOS sensors), Figaro TGS3870 MOS sensors, and the like.

In any of the prior examples, the devices could be configured with proximity sensors requiring the subject to be within a fixed distance such as 20 feet, or ten feet, or more preferably within five feet or less.

Alternatively, the components could be configured with a programmable code which must be entered periodically for activation. Still further the components could be hard wired with a timing circuit that requires a minimal period of time between uses for activation.

In addition, the device could be configured as shown in FIG. 6 with a base having hardware and software for the transmission of collected data as previously described.

Provided herein is a method of treating a first subject addicted to a tobacco product, the method comprising administering to the first subject who has previously failed nicotine replacement therapy, a modified risk product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by or an employee of a convenience or retail store.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by or an employee of a convenience or retail store.

Provided herein is a method of treating a first subject addicted to a tobacco product, the method comprising administering to the first subject a modified risk product or other tobacco product only after at least one failed attempt by the first subject to quit using such tobacco product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by an employee of a convenience or retail store.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method of treating a first subject addicted to a tobacco product, the method comprising administering a modified risk product or other tobacco product to the first subject only after the modified risk product or other tobacco product is prescribed to the first subject.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the modified risk product or other tobacco product is prescribed and administered by a physician, a nurse, a pharmacist, or an accredited healthcare provider.

In some embodiments, the product is administered by an accredited employee of a convenience or retail store, or an employee of an accredited convenience or retail store.

In some embodiments, the product is administered by an internet or wireless based application, service or business.

In some embodiments, the product is administered by a call center or phone based application service or business.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method for increasing the likelihood that the first subject or a second subject will stop using the tobacco product.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As a result of having performed the compliance verification testing, subjects are more likely to be interested in the outcomes and act on those results, including increasing the likelihood that the first subject or a second subject will stop using the tobacco product.

Provided herein is a method for decreasing the likelihood that a second subject not using the tobacco product will start using the tobacco product. FIGS. 4 and 5 are both illustrations of how a second user would be prevented from acquiring and using a modified risk tobacco product, hence, reducing the likelihood of starting to use the tobacco product.

Provided herein is a method for verifying the at least one prior failed attempt to stop using tobacco products prior to the modified risk product or other tobacco product being provided to a first subject.

Provided herein is a method for verifying that a first subject meets at least one eligibility requirement for use of a modified tobacco risk product, as illustrated by FIGS. 3A & 3B.

Provided herein is a method for verifying a subject's eligibility requirement comprising: possession of an eligibility card, meeting qualifications for the eligibility card, possessing a valid verification code, possessing a physician-provided eligibility record, possessing a pharmacist-provided eligibility record, passing a pharmacist-provided eligibility evaluation, as illustrated by FIG. 4.

In some embodiments of a method having an eligibility requirement, the identity verification step comprises at least one of:
  evidence of a minimum age requirement,
  evidence of a previously failed nicotine replacement therapy, and
  evidence of a at least one failed attempt by the patient to quit using such tobacco product,
  electronic or telephonic verification of a unique subject eligibility card or code identifier,
  software verification of a unique subject eligibility card or code identifier,
  electronic fingerprint verification of an eligible subject,
  an activation code, or
  an electronic dongle, electronic security key fob, or equivalent.

Provided herein is a method for verifying a subject's eligibility requirement wherein the verifying step is performed by a physician, a nurse, a pharmacist, or an accredited healthcare provider.

In some embodiments, the verifying a subject's eligibility requirement is performed by an accredited employee of a convenience or retail store, or by an employee of an accredited convenience or retail store.

In some embodiments, the verifying a subject's eligibility requirement is performed by an internet or wireless based application, service or business.

In some embodiments, the verifying a subject's eligibility requirement is performed by an internet or wireless based application, service or business.

Provided herein is a method for providing a prescription for a modified risk product, wherein said prescription is provided by a qualified healthcare provider.

Provided herein is a method of monitoring compliance of a first subject addicted to a tobacco product, and provided with a modified risk product, the method comprising, measuring nicotine levels, nicotine levels, CO levels, or other biomarker levels of a first subject prior to administration of said modified risk product or other tobacco product and routine measurement after administration of said modified risk product, and comparing said prior nicotine levels, nicotine levels, CO levels, or other biomarker levels to anticipated nicotine levels, nicotine levels, CO levels, or other biomarker levels of the first subject after administration of said modified risk product.

In some embodiments the method of monitoring compliance comprises; measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva or urine samples, as illustrated in FIG. 7, or measuring nicotine levels, nicotine levels, CO levels, or other biomarker levels in hair samples.

Provided herein is a method of monitoring compliance of a first subject addicted to a tobacco product, and provided with a modified risk product, the method comprising, measuring nicotine levels consumed by a first subject prior to administration of said modified risk product or other tobacco product and routine measurement of nicotine levels consumed after administration of said modified risk product, and comparing said prior nicotine levels to anticipated nicotine levels of the first subject after administration of said modified risk product. Numerous methods can be devised as evidence herein, and further illustrated by one example as shown in FIG. 6.

In some embodiments, a method of monitoring comprises; using an electronic signature to track the pattern of use of a vaporizer, electronic cigarette, or other modified risk product or other tobacco product wherein said product transmits a record of use over a given period of time.

In some embodiments, a record of use comprises levels of nicotine consumed, times, and dates it was consumed.

In some embodiments, the record of use is stored to a data storage device and later downloaded for use by a qualified healthcare provider.

In some embodiments, the record of use is transmitted wirelessly to a data storage device and later downloaded for use by a qualified healthcare provider.

In some embodiments, the record of use is stored within the device, and later downloaded for use by a qualified healthcare provider.

Provided herein is a method of monitoring the use of a modified risk product or other tobacco product by a first subject addicted to a tobacco product, the method comprising, requiring an identification recognition system be activated before use of a modified risk product or other tobacco product can take place.

In some embodiments, the identification recognition system comprises, a fingerprint scanner, a lip print scanner, face recognition, a retinal scan, a combination code, an activation code, security key fob, or dongle.

In some embodiments, the identification recognition system comprises an electronic application for a smartphone, laptop, desktop, or tablet computing device, capable of communicating with the modified risk product or other tobacco product by a Bluetooth or wireless communication system.

In some embodiments, the identification recognition system must be within a fixed distance of the modified risk product or other tobacco product for product to continue to work.

In some embodiments, the identification recognition system must be within 20 feet of the modified risk product.

In some embodiments, the identification recognition system must be within 10 feet of the modified risk product.

In some embodiments, the identification recognition system must be within 5 feet of the modified risk product.

Provided herein is a method of risk mitigation wherein the potential risk of misuse or abuse of a modified risk product or other tobacco product may be present and require a distinct form of compliance monitoring.

For example, an addicted subject may continue to use the first tobacco product after being provided the modified risk product, thus increasing the potential risk for one or more tobacco related diseases or exposure to one or more harmful substances.

In some embodiments, monitoring for misuse or abuse of a modified risk product or other tobacco product comprises measuring nicotine levels consumed by a first subject prior to administration of said modified risk product or other tobacco product and routine measurement of nicotine levels consumed after administration of said modified risk product, and comparing said prior nicotine levels to anticipated nicotine levels of the first subject after administration of said modified risk product.

For example, if an investigator suspected that the subject was continuing to use cigarettes after receiving a modified risk product, the results of additional nicotine in the subject's system would be a relatively simple calculation. An example of this calculation could be: [Nicotine or cotinine from cigarettes]=[amount measured in blood or saliva]−[amount reported as dispensed by modified risk device]. It is understood that a similar calculation could be derived from any comparable nicotine/cotinine test regardless of the testing method, provided testing methods were consistent and/or interchangeable.

In some embodiments, multiple compliance verification and tracking systems could be combined and randomly or non-randomly applied as part of a REMS program. For example, results of a subject's nicotine level, nicotine levels, CO level, or other biomarker level testing could be compared to prior results (FIG. 7), in addition to remotely monitoring transmitted usage patterns of the modified risk product or other tobacco product (FIG. 6). Upon comparison, a skilled health professional could determine if abuse or misuse is potentially occurring.

Provided herein is a method of protecting the public health comprising increasing the likelihood that a first subject or a second subject will stop using a tobacco product by providing a modified risk product or other tobacco product for administration to the first subject addicted to the tobacco product wherein the modified risk product or other tobacco product provides a faster onset of nicotine delivery, or a higher peak level of nicotine delivery.

Provided herein is a method of risk mitigation wherein the potential risk of misuse or abuse of a modified risk product or other tobacco product is ranked or stratified in comparison to other tobacco products.

In some embodiments, the relative potential risk of the modified risk product or other tobacco product is determined by comparing the pharmacokinetic profile of the modified risk product or other tobacco product to nicotine.

In some embodiments the pharmacokinetic profile of the modified risk product or other tobacco product is determined by the maximum plasma concentration (Cmax) of nicotine, compared to a cigarette.

In some embodiments the pharmacokinetic profile of the modified risk product or other tobacco product is determined by the time after administration of the product for nicotine to reach maximum plasma concentration (Tmax), compared to a cigarette.

In some embodiments the pharmacokinetic profile of the modified risk product or other tobacco product is determined by the rate-of-increase of nicotine delivery or concentration in the plasma of a subject compared to a cigarette.

In some embodiments, the relative potential risk of the modified risk product or other tobacco product is determined by comparing the nicotine concentration of the modified risk product or other tobacco product other nicotine products in the market.

In some embodiments, the relative potential risk of the modified risk product or other tobacco product is ranked by ease of access associated with the prescriber/administrator.

In some embodiments, the relative potential risk of the modified risk product or other tobacco product is ranked by ease of access through various distribution channels.

In some embodiments the modified risk product or other tobacco product comprises vaporizing tobacco leaves or finely chopped tobacco below their pyrolytic temperature.

In some embodiments the modified risk product or other tobacco product comprises heating tobacco leaves or finely chopped tobacco below their pyrolytic temperature.

In some embodiments the modified risk product or other tobacco product comprises vaporization of a nicotine salt.

In some embodiments the modified risk product or other tobacco product comprises heating of a nicotine salt below its pyrolytic temperature.

Provided herein is a method of validating the effectiveness of a modified risk product or other tobacco product used with a Risk Evaluation and Mitigation Strategy comprising: collecting and sending a subject's samples taken before (and/or in some variations, after) being provided a modified risk product, for analysis to an accredited testing facility, measuring the difference between samples for nicotine levels, nicotine levels, CO levels, or other biomarker levels in blood, expelled breath, saliva, hair, and/or urine, and performing an appropriate analysis to determine if the modified risk product or other tobacco product met the goals of the Risk Evaluation and Mitigation Strategy.

In some embodiments, components of the validation process may be performed by a physician, a nurse, a pharmacist, an accredited healthcare provider, or an employee of a convenience or retail store or an accredited testing facility.

Provided herein is a method of protecting the public health wherein the provider of a modified risk product is subject to a compliance verification system.

In some embodiments, the provider verification is performed by an independent auditor.

Provided herein is a system for verification, tracking, and reporting use of a modified risk product comprising: an electronic cigarette, an electronic pipe, an electronic cigar, an electronic water pipe, an electronic vaporizer, and a tobacco or nicotine product, comprising a battery, an atomizer, electronic circuitry, a memory storage device for tracking components of usage activity, a means of memory transfer, and a charging circuit, a charger base station comprising a memory storage device, a means for receiving data from said modified risk product memory storage device and transmitting said data to a third party, activation software for recognition of a specific device, keyed to said charger base, capable of interfacing with an external device, wherein said external device comprises; a smart phone, computer, electronic fob, electronic dongle, and a Bluetooth or wireless device.

In some embodiments, the system is used in combination with a risk evaluation and mitigation strategy.

In some embodiments, the system comprises activation means, for recognition and verification of a subject to establish user eligibility prior to use.

In some embodiments, the system comprises activation means, for recognition and verification of a subject to establish user eligibility prior to use.

In some embodiments, the system is used to verify subject compliance for use of a modified risk product. In some embodiments the system comprises a means for validating overall success of the risk mitigation product when used with the risk evaluation and mitigation strategies While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
 measuring, via a diagnostic test using an electrochemical or metal oxide semiconductor (MOS) sensor, a concentration of nicotine in a sample of a breath of a user of an electronic vaporizer;

comparing, via electronic circuitry, the concentration of nicotine to a threshold; and enabling or disabling, via the electronic circuitry, operation of the electronic vaporizer based on the comparison of the concentration of nicotine to the threshold, in accordance with a risk evaluation and mitigation strategy (REMS) protocol to prevent unauthorized usage of the electronic vaporizer.

2. The method of claim 1, wherein the enabling operation of the electronic vaporizer is performed when the concentration of nicotine in the sample of breath of the user is above the threshold.

3. The method of claim 1, wherein the enabling operation of the electronic vaporizer is performed when the concentration of nicotine in the sample of breath of the user is below the threshold.

4. The method of claim 1, wherein the threshold corresponds to a concentration of nicotine associated with an expected nicotine user.

5. The method of claim 1, wherein the threshold corresponds to a concentration of nicotine indicative of whether the user has consumed a nicotine product within the last twenty-four hours.

6. The method of claim 1, further comprising sampling, via a sensor, the sample of the breath of the user.

7. The method of claim 6, wherein the sensor comprises an electromechanical sensor.

8. A vaporizer device, comprising:
   a sensor configured to sample a breath of a user of the vaporizer device; and
   electronic circuitry configured to perform operations comprising:
      determining a concentration of nicotine using an electrochemical or metal oxide semiconductor (MOS) sensor in the sample of the breath of the user based on a diagnostic test,
      comparing the concentration of nicotine to a threshold, and
      enabling operation of the vaporizer device based on the comparison of the concentration of nicotine to the threshold, wherein the electronic circuitry adjusts vaporizer settings to optimize delivery.

9. The vaporizer device of claim 8, further comprising a mouthpiece, wherein the sensor is disposed on the mouthpiece.

10. The vaporizer device of claim 8, wherein the enabling operation of the vaporizer device is performed when the concentration of nicotine in the sample of breath of the user is above the threshold.

11. The vaporizer device of claim 8, wherein the enabling operation of the vaporizer device is performed when the concentration of nicotine in the sample of breath of the user is below the threshold.

12. The vaporizer device of claim 8, wherein the sensor comprises an electrochemical sensor.

13. The vaporizer device of claim 8, wherein the threshold corresponds to a concentration of nicotine associated with an expected nicotine user.

14. The vaporizer device of claim 8, wherein the threshold corresponds to a concentration of nicotine indicative of whether the user has consumed a nicotine product within the last twenty-four hours.

* * * * *

UNITED STATES PATENT AND TRADEMARK OFFICE
CERTIFICATE OF CORRECTION

PATENT NO. : 12,232,540 B2
APPLICATION NO. : 17/520032
DATED : February 25, 2025
INVENTOR(S) : Gal A. Cohen Page 1 of 1

It is certified that error appears in the above-identified patent and that said Letters Patent is hereby corrected as shown below:

In the Claims

At Column 44, Claim 8, Line 9, after "enabling" insert -- or disabling --.

At Column 44, Claim 8, Lines 11-12, delete "wherein the electronic circuitry adjusts vaporizer settings to optimize delivery" and insert -- in accordance with a risk evaluation and mitigation strategy (REMS) protocol to prevent unauthorized usage of the vaporizer device. --.

Signed and Sealed this
Twenty-fourth Day of June, 2025

Coke Morgan Stewart
*Acting Director of the United States Patent and Trademark Office*